(12) United States Patent
Piferi et al.

(10) Patent No.: US 10,357,281 B2
(45) Date of Patent: Jul. 23, 2019

(54) SPLIT-GUIDES FOR TRAJECTORY FRAMES FOR MEDICAL INTERVENTIONAL SYSTEMS AND METHODS

(71) Applicant: MRI Interventions, Inc., Irvine, CA (US)

(72) Inventors: Peter Piferi, Orange, CA (US); Jesse Flores, Perris, CA (US); Rajesh Pandey, Irvine, CA (US)

(73) Assignee: MRI Interventions, Inc., Irvine, CA (US)

( * ) Notice: Subject to any disclaimer, the term of this patent is extended or adjusted under 35 U.S.C. 154(b) by 406 days.

(21) Appl. No.: 14/829,708

(22) Filed: Aug. 19, 2015

(65) Prior Publication Data
US 2016/0100895 A1  Apr. 14, 2016

Related U.S. Application Data

(60) Provisional application No. 62/059,225, filed on Oct. 3, 2014.

(51) Int. Cl.
| | |
|---|---|
| *A61B 17/34* | (2006.01) |
| *A61B 17/00* | (2006.01) |
| *A61B 90/11* | (2016.01) |
| *A61B 34/20* | (2016.01) |
| *A61N 1/05* | (2006.01) |
| *A61B 90/10* | (2016.01) |

(52) U.S. Cl.
CPC .......... *A61B 17/3421* (2013.01); *A61B 17/00* (2013.01); *A61B 34/20* (2016.02); *A61B 90/11* (2016.02); *A61B 2017/3407* (2013.01); *A61B 2034/2055* (2016.02); *A61B 2090/103* (2016.02); *A61N 1/0529* (2013.01)

(58) Field of Classification Search
CPC ................ A61B 17/3421; A61B 90/11; A61B 2017/3407; A61B 2090/103; A61B 17/00; A61B 34/20; A61B 2034/2055; A61N 1/0529
USPC .......................................... 600/427; 606/130
See application file for complete search history.

(56) References Cited

U.S. PATENT DOCUMENTS

| | | | |
|---|---|---|---|
| 4,838,506 A * | 6/1989 | Cooper | A61B 8/12 248/200 |
| 5,116,345 A | 5/1992 | Jewell et al. | |
| 6,050,992 A | 4/2000 | Nichols | |
| 6,167,311 A | 12/2000 | Rezai | |
| 6,356,786 B1 | 3/2002 | Rezai et al. | |
| 6,405,079 B1 | 6/2002 | Ansarinia | |
| 6,438,423 B1 | 8/2002 | Rezai et al. | |

(Continued)

*Primary Examiner* — George J Ulsh
(74) *Attorney, Agent, or Firm* — Myers Bigel, P.A.

(57) ABSTRACT

Surgical devices such as a device guide for a trajectory frame for image-guided procedures, is configured with first and second elongate and cooperating semi-circular members that together define a longitudinally extending open channel and that can separate along longitudinally extending split lines into discrete first and second elongate semicircular members. The surgical devices with the first and second semi-circular members can include a device guide and dock and lock inserts that are detachably held by dock and lock members to a guide support column that also concurrently holds the device guide during at least part of an image guided procedure.

17 Claims, 26 Drawing Sheets
(4 of 26 Drawing Sheet(s) Filed in Color)

(56) References Cited

U.S. PATENT DOCUMENTS

| | | |
|---|---|---|
| 6,526,318 B1 | 2/2003 | Ansarinia |
| 6,539,263 B1 | 3/2003 | Schiff et al. |
| 6,609,030 B1 | 8/2003 | Rezai et al. |
| 6,708,064 B2 | 3/2004 | Rezai |
| 8,374,677 B2 | 2/2013 | Piferi et al. |
| 2007/0167930 A1* | 7/2007 | Eversull ............ A61M 25/0668 604/524 |
| 2014/0024927 A1 | 1/2014 | Piferi |
| 2015/0080851 A1* | 3/2015 | Kurth ................ A61M 25/0097 604/507 |

* cited by examiner

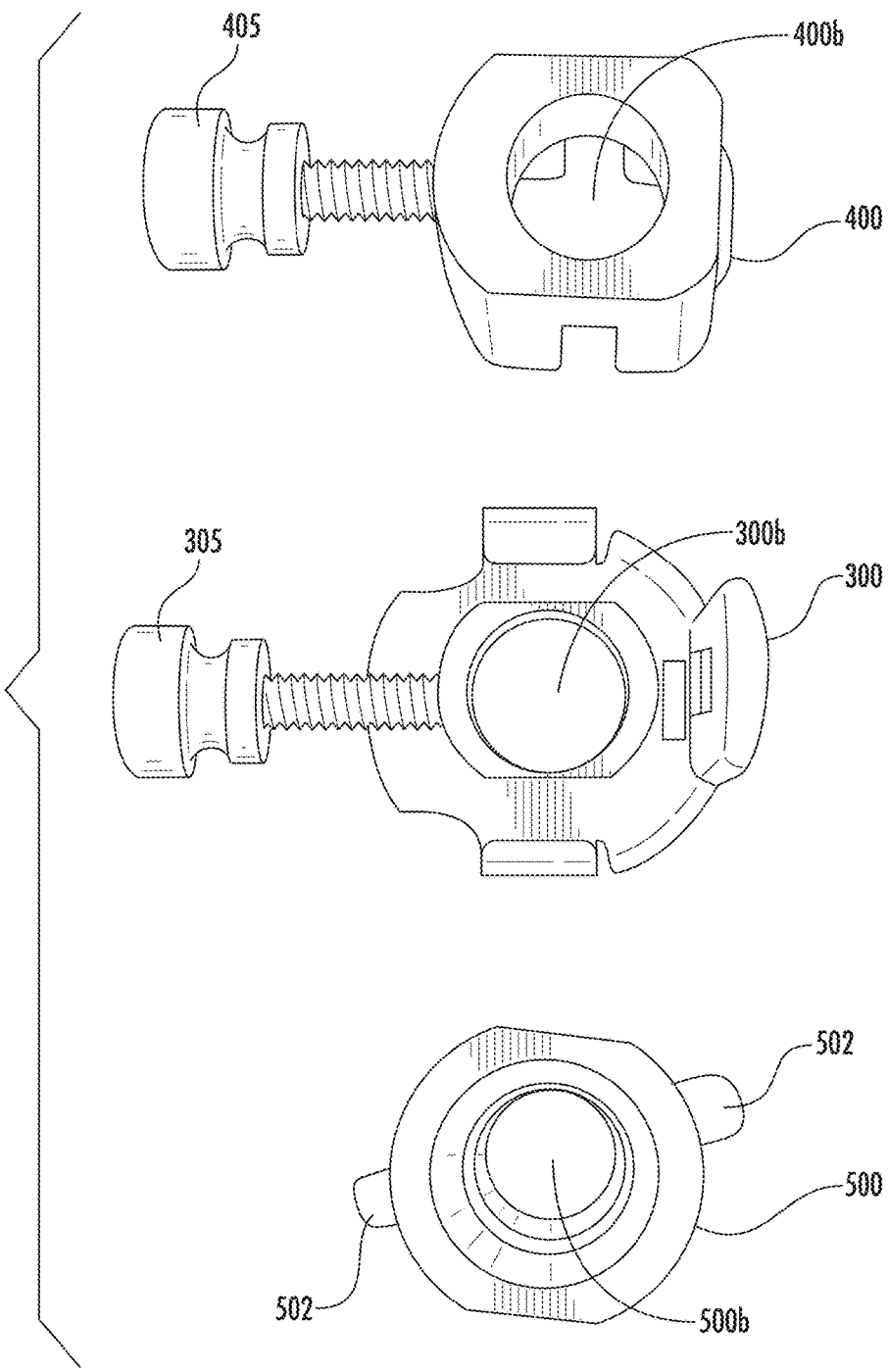

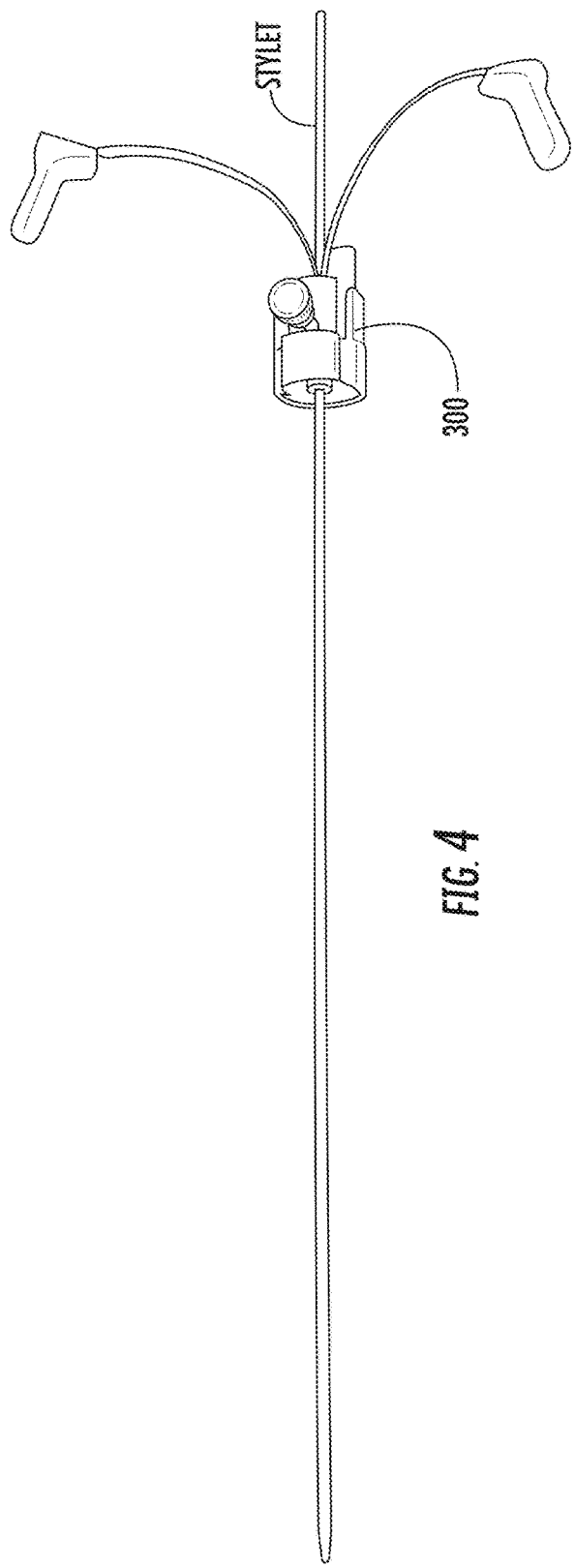

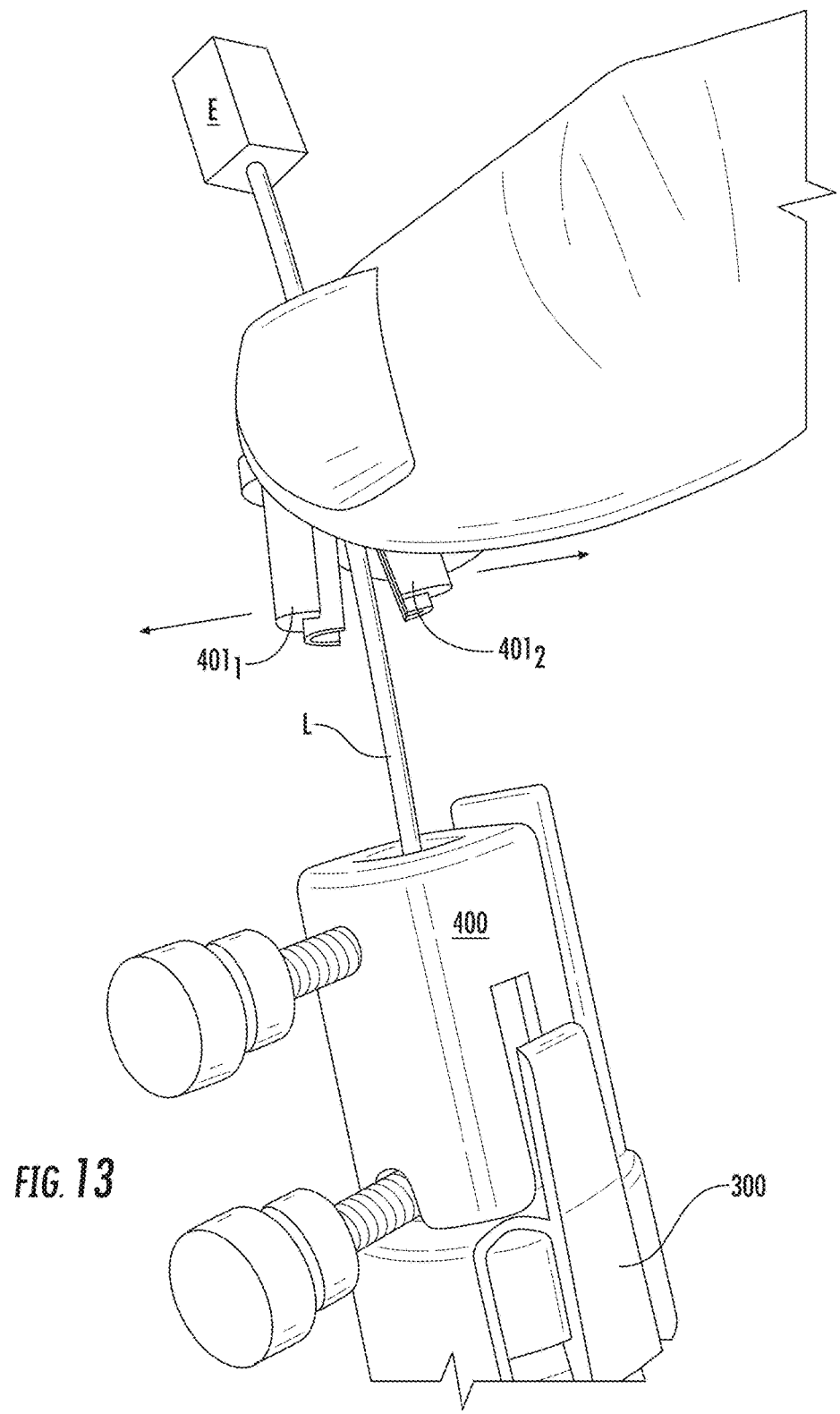

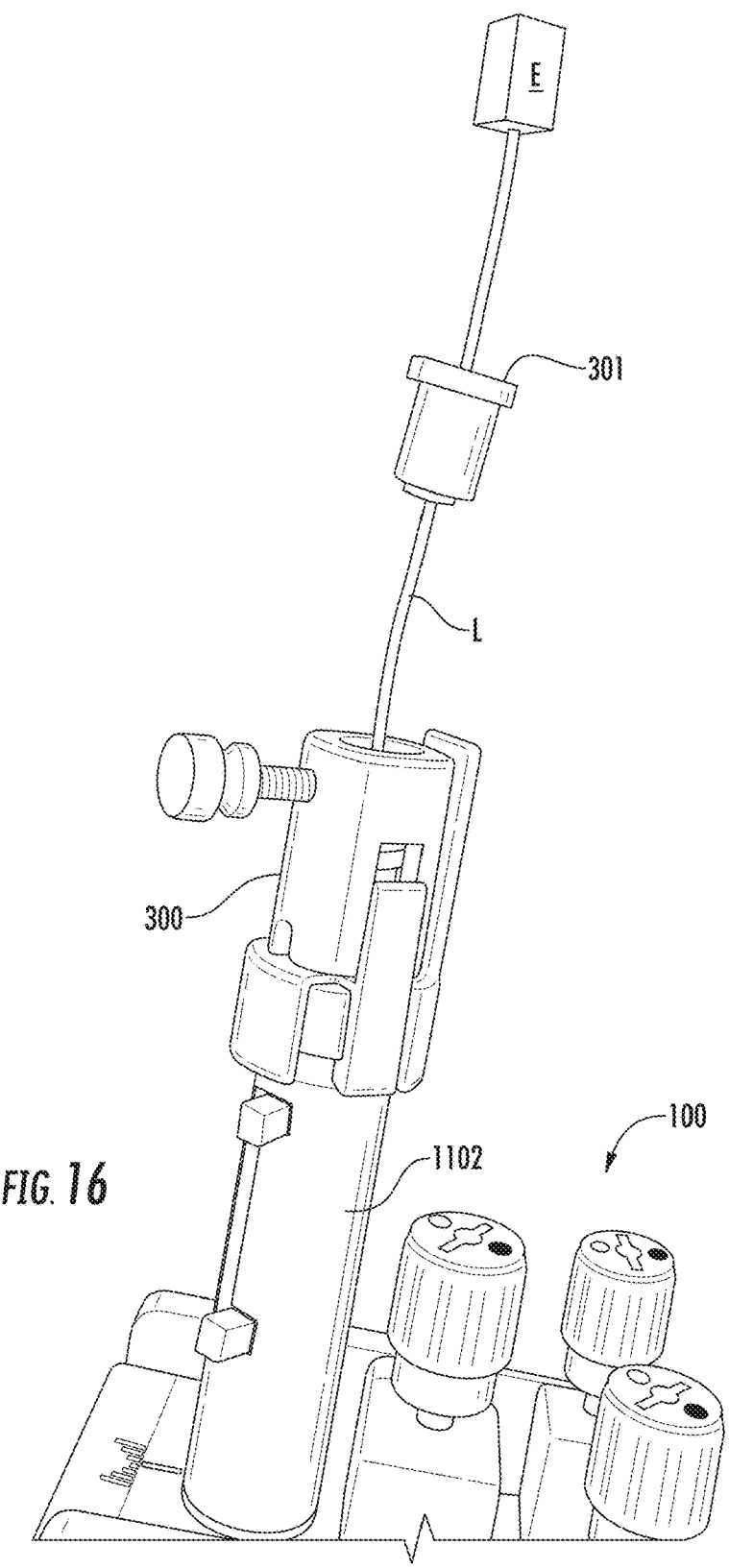

SPLIT-GUIDES FOR TRAJECTORY FRAMES FOR MEDICAL INTERVENTIONAL SYSTEMS AND METHODS

RELATED APPLICATIONS

This application claims priority to and the benefit of U.S. Provisional Application Ser. No. 62/059,225, filed Oct. 3, 2014, the contents of which are hereby incorporated by reference as if recited in full herein.

FIELD OF THE INVENTION

The present invention relates generally to medical systems and methods and, more particularly, to in vivo medical systems and methods.

BACKGROUND

During image-guided surgeries, it can be desired to insert or implant interventional devices in the body using trajectory frames for defining intrabody trajectories to define a surgical path.

SUMMARY

Embodiments of the present invention provide methods, devices and systems for localized placement and/or delivery of diagnostic or therapeutic devices or substances which can be delivered with a trajectory frame, e.g., leads with integrated electronic packages with large numbers of electrode connections with corresponding implantable leads which can be held in a single conduit that merge into distal implantable electrodes. The multiple electrodes can be, for example, 32, 48, 64, or 128 or even more, in contrast to conventional numbers which are typically about 4.

To allow the trajectory frame and cooperating components to be more easily removed post-implantation, one or more of the surgical devices (e.g., a device guide) can have a split body configuration.

One or both of the lock and dock components can hold lock and dock inserts that can have split body configurations.

Embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain.

Embodiments of the present invention may be suitable for a number of interventional procedures in many locations inside the body including, but not limited to, brain, cardiac, spinal, urethral, and the like.

Embodiments of the present invention may be suitable for a number of image guided procedures, including CT and/or MRI-guided electrode delivery, and/or drug delivery procedures, to intra-brain or other intra-body targeted locations.

According to some embodiments of the present invention, the trajectory frame includes a base, a yoke movably mounted to the base and that is rotatable about a roll axis, and a platform movably mounted to the yoke and that is rotatable about a pitch axis. The platform includes an X-Y support table that is configured to move in an X-direction and Y-direction relative to the platform. The base has a patient access aperture formed therein, and is configured to be secured to the body of a patient such that the aperture overlies an opening in the body. A roll actuator is operably connected to the yoke and is configured to rotate the yoke about the roll axis. A pitch actuator is operably connected to the platform and is configured to rotate the platform about the pitch axis. An X-direction actuator is operably connected to the platform and is configured to move the X-Y support table in the X-direction. A Y-direction actuator is operably connected to the platform and is configured to move the X-Y support table in the Y-direction.

A tubular guide support (e.g., support column) extends through the platform along a Z-direction and includes opposite proximal and distal end portions. The guide support releasably holds a device guide with a distal end portion that is positioned proximate the patient access aperture. The device guide includes a bore therethrough that is smaller than the guide support bore and that extends from the proximal end portion to the distal end portion. The device guide has cooperating first and second segments that can be separated along a longitudinally extending split line or lines.

Embodiments of the invention are directed to a surgical device guide that includes first and second elongate semi-circular members that cooperate to define a longitudinally extending open channel and that separate along longitudinally extending split lines into discrete first and second elongate semicircular members.

The surgical device guide can be in combination with a guide support configured to be secured to a platform of a trajectory frame assembly, wherein the guide support comprises opposite proximal and distal end portions. The guide support can have a bore therethrough that extends from the proximal end portion to the distal end portion.

The surgical device can be in combination with a lock member and a dock member configured to attach (directly and/or indirectly) to a device guide support. The lock member can include an insert with first and second semi-circular detachable members. The dock member can configured to attach to a device guide support. The dock member can include an insert with first and second semi-circular detachable members.

The open channel can have a diameter of between about 2-3 mm (e.g., about 2 mm, about 2.25 mm, about 2.5 mm, about 2.75 mm and about 3 mm).

The first and second semi-circular members can have an outer wall with edges thereof being planar and configured to releasably abut each other to encircle the through channel.

Other embodiments are directed to a trajectory frame assembly. The assembly can include a base having a patient access aperture formed therein. The base is configured to be secured to the body of a patient. The assembly can include a yoke movably mounted to the base and rotatable about a roll axis and a platform movably mounted to the yoke and rotatable about a pitch axis; an elongated device guide support secured to the platform. The guide can include opposite proximal and distal end portions and a bore therethrough that extends from the proximal end portion to the distal end portion. The assembly can include a lock member attached to the device guide support and a dock member attached to the device guide support. The assembly can also include a device guide extending through the device guide support. The device guide can have two elongate cooperating members that define a longitudinally extending through-channel when held in the device guide support and that can laterally separate from each other along longitudinally split lines upon removal from the device guide support.

The lock member can include an insert that has first and second releasably attached segments that form a longitudinally extending open channel when attached together.

The dock member can include an insert that has first and second releasably attached segments that form a longitudinally extending open channel when attached together.

Other aspects of the invention are directed to an elongate device guide for a trajectory frame for an image guided surgical procedure. The elongate device guide can have first and second longitudinally extending members that form a longitudinally extending open channel when positioned proximate each other and that can separate along a pair of diametrically opposed longitudinally extending (pre-formed split) lines.

The first and second members can have walls that are arcuate with edges thereof being planar, wherein the planar edges are configured to releasably abut each other. The channel can have a diameter of between about 1-6 mm.

The channel can optionally have a diameter of between about 2-3 mm, inclusive thereof.

Some embodiments are directed to surgical assemblies for an image guided surgery. The assemblies include a device guide support adapted to attach to a trajectory guide frame, the device guide support having a cylindrical, longitudinally extending open channel. The assemblies also include a dock member configured to engage the trajectory guide support and a lock member configured to attach to the dock member above the device guide support. The assemblies can also include a removable guide support cap configured to attach to a top of the device guide support under the dock member. The lock member and dock member can each include inserts with cooperating first and second longitudinally extending members that define an open longitudinally extending channel and that can separate from each other when removed from the trajectory guide support, optionally along pre-formed longitudinally extending split lines.

The assembly can include a device guide held in the trajectory guide support. The device guide support can include first and second longitudinally members with an arcuate inner wall with planar outer edges that cooperate to define an open longitudinally extending through-channel when held in the device guide support, wherein the planar edges are configured to releasably abut each other. The channel can have a diameter of between about 1-6 mm.

The channel can have a diameter of between about 2-3 mm.

Some embodiments are directed to a trajectory frame assembly with a trajectory frame that has a tubular device guide support that extends through a platform of the trajectory frame along a Z-direction and includes opposite proximal and distal end portions. The device guide support releasably holds a device guide with a distal end portion that is positioned proximate the patient access aperture. The device guide includes a bore therethrough that is smaller than the device guide support bore and that extends from the proximal end portion to the distal end portion. The device guide is rigid and has cooperating first and second segments that can be separated along longitudinally extending split lines.

The first and second segments of the device guide can cooperate and face each other to define a through channel with a diameter of between about 1-6 mm.

The through channel can have a diameter of between about 2-3 mm.

Some embodiments are directed to methods of implanting a device such as a lead in a patient. The methods include: (a) providing a trajectory frame with an elongated guide support releasably holding a device guide; (b) guiding placement of an implantable device (e.g., lead with a plurality of electrodes) to a desired interbody location using the trajectory frame; (c) inserting the device through the device guide and into the patient at the desired interbody location; and then slidably removing the device guide out of the guide support and separating the device guide into first and second longitudinally extending members.

The guide support can have a dock attached to the guide support and a lock attached to the dock to hold the dock to the guide support. The dock and lock can each include a respective insert with first and second cooperating, detachable and longitudinally extending members. The method can include, before the step of slidably removing the device guide, slidably removing the lock insert from the lock and separating the first and second cooperating members thereof, then slidably removing the dock insert from the dock and separating the first and second cooperating members thereof.

The implantable device can be an implantable lead with a plurality of electrodes, typically greater than four and less than 200, such as about 32, about 48, about 64, or about 128.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3 is a top view of a dock member, lock member and removable guide support cap all having relatively large through inner diameters according to embodiments of the present invention.

FIG. 4 is a side perspective view of the dock member and dock insert with a stylet and sheath extending therethrough according to embodiments of the present invention.

FIG. 5A is a line drawing of a corresponding photograph shown in FIG. 5B.

FIG. 6A is a line drawing of a corresponding photograph shown in FIG. 6B.

FIG. 10A is a line drawing of a corresponding photograph shown in FIG. 10B.

FIGS. 12-22 show exemplary sequences of post-lead placement to remove a trajectory frame and cooperating components (although shown in the figures, the sheath is not typically in position during this sequence) so as to accommodate a relatively large electronics package on the lead according to embodiments of the present invention.

DETAILED DESCRIPTION

Figure 1:
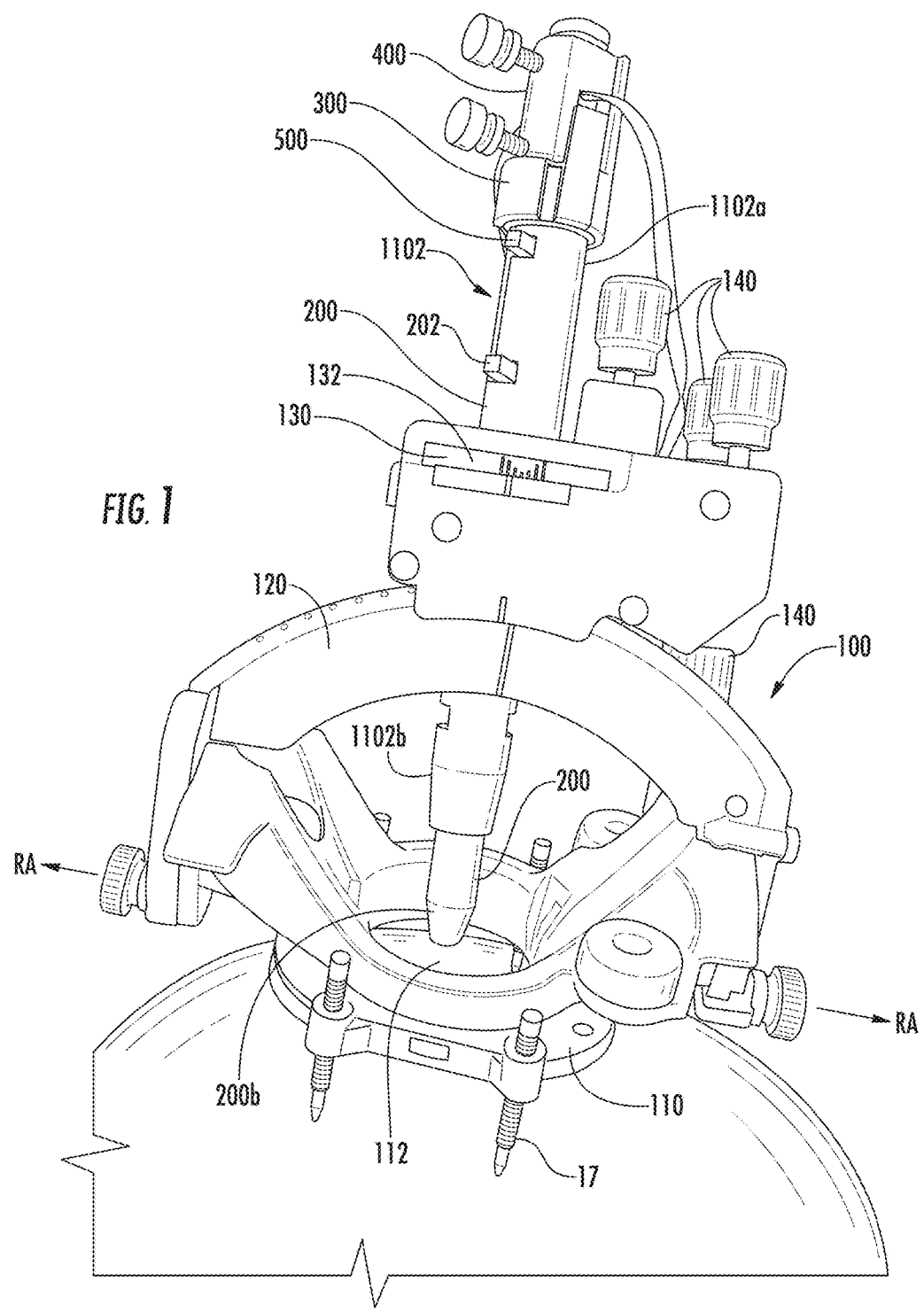
FIG. 1 is an enlarged side perspective view of an exemplary trajectory frame assembly according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The abbreviations "FIG. and "Fig.") for the word "Figure" can be used interchangeably in the text and figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/−twenty percent (20%).

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

Thus, the term "cannula" refers to an elongate device that can be associated with a trajectory frame that attaches to a patient, but does not necessarily enter the body of a patient.

The term "imaging coils" refers to a device that is configured to operate as an MRI receive antenna. The term "coil" with respect to imaging coils is not limited to a coil shape but is used generically to refer to MRI antenna configurations, loopless, looped, etc., as are known to those of skill in the art. The term "fluid-filled" means that the component includes an amount of the fluid but does not require that the fluid totally, or even substantially, fill the component or a space associated with the component. The fluid may be an aqueous solution, MR contrast agent, or any material that generates MRI signal.

The term "two degrees of freedom" means that a trajectory frame described herein allows for at least translational (swivel or tilt) and rotational movement over a fixed site, which may be referred to as a Remote Center of Motion (RCM).

Embodiments of the present invention can be configured to guide and/or place diagnostic or interventional devices and/or therapies to any desired internal region of the body or object. The object can be any object, and may be particularly suitable for animal and/or human subjects. Some embodiments can be sized and configured to place implantable DBS leads for brain stimulation, typically deep brain stimulation. Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc. In some embodiments, the trajectory frame and/or interventional tools can be configured to facilitate high resolution imaging via integral intrabody imaging coils (receive antennas), high intensity focused ultrasound (HIFU), and/or the interventional tools can be configured to stimulate local tissue, which can facilitate confirmation of proper location by generating a physiologic feedback (which may optionally be observed physical reaction or via fMRI).

Some embodiments can be used to deliver bions, stem cells or other target cells to site-specific regions in the body, such as neurological target sites and the like. In some embodiments, the systems deliver stem cells and/or other cardio-rebuilding cells or products into cardiac tissue, such as a heart wall via a minimally invasive image guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Generally stated, some embodiments of the invention are directed to image guided interventional procedures and provide interventional tools and/or therapies that may be used to locally place interventional tools or therapies in vivo to site-specific regions using any suitable navigation system and/or imaging modality, such as but not limited to an MRI system. The interventional tools can be used to define an image guided trajectory or access path to an in vivo treatment site.

Some embodiments of the invention provide trajectory frames and/or interventional tools that can provide positional data regarding location and orientation of a tool in 3-D space with a visual confirmation on an MRI or CT image or other surgical navigation system, including, but not limited to camera and reflective optical fiducials and/or electromagnetic tracking systems.

Embodiments of the invention may provide an integrated system that may allow physicians to place interventional devices/leads and/or therapies accurately and in shorter duration procedures over conventional systems (typically under six hours for DBS implantation procedures, such as between about 1-5 hours).

Embodiments of the present invention will now be described in detail below with reference to the figures.

FIG. 1 shows an exemplary trajectory frame 100 that is configured to be mounted to a patient's skull around a burr hole ring and over a burr hole to provide a stable platform for advancing surgical devices, leads, etc. in the brain. The trajectory frame 100 includes a base 110, a yoke 120, a platform 130, and a plurality of actuators 140. The base 110 has a patient access aperture 112 formed therein, as illustrated. The base 110 is configured to be secured (directly or indirectly) to the skull or scalp of a patient such that the patient access aperture 112 overlies the burr hole 10 in the patient skull. The trajectory frame may be mounted to cooperating devices and/or to other locations about a patient's body.

The yoke 120 can be movably mounted to the base 110 and is rotatable about a roll axis. A roll actuator 140a is operably connected to the yoke 120 and is configured to rotate the yoke 120 about the roll axis. A pitch actuator 140 is operably connected to the platform 130 and is configured to rotate the platform 130 about the pitch axis. The illustrated platform 130 includes an X-Y support table 132 that is movably mounted to the platform 130. The X-Y support table 132 is configured to move in an X-direction and Y-direction relative to the platform 130 and relative to a Z-direction defined by the longitudinal axis of the device guide support 1102. An X-direction actuator 140 is operably connected to the platform 130 and is configured to move the X-Y support table 132 in the X-direction. A Y-direction actuator 140 is operably connected to the platform 130 and is configured to move the X-Y support table 132 in the Y-direction. A pitch actuator 140 is operably connected to the platform 130 and is configured to rotate the platform 130 about the pitch axis. See, e.g., U.S. Patent Application Publication No. 2014/0024927 for further description of exemplary trajectory frame assemblies.

The actuators 140 are configured to translate and/or rotate portions of the trajectory frame 100. The device guide support 1102 is configured to translate in response to translational movement of the X-Y support table 132 and to rotate in response to rotational movement of the yoke 120 and platform 130 to define different axial intrabody trajectories extending through the patient access aperture 112 in the frame base 110.

The device guide support 1102 can be configured to removably receive various probes and/or tools including a device guide 200 for guiding placement of an intrabody device such as a needle or an implantable DBS lead L (simulated lead shown in FIG. 11) as shown in FIG. 1. The guide 1102 may have a larger diameter than conventional targeting cannula guides which thereby allows for various devices to be utilized with the trajectory frame 100 that otherwise would not be able to do so. In some particular embodiments, the device guide support 1102 has a bore size (e.g., diameter) that is between about 7-10 mm, typically about 8 mm.

Figure 23:
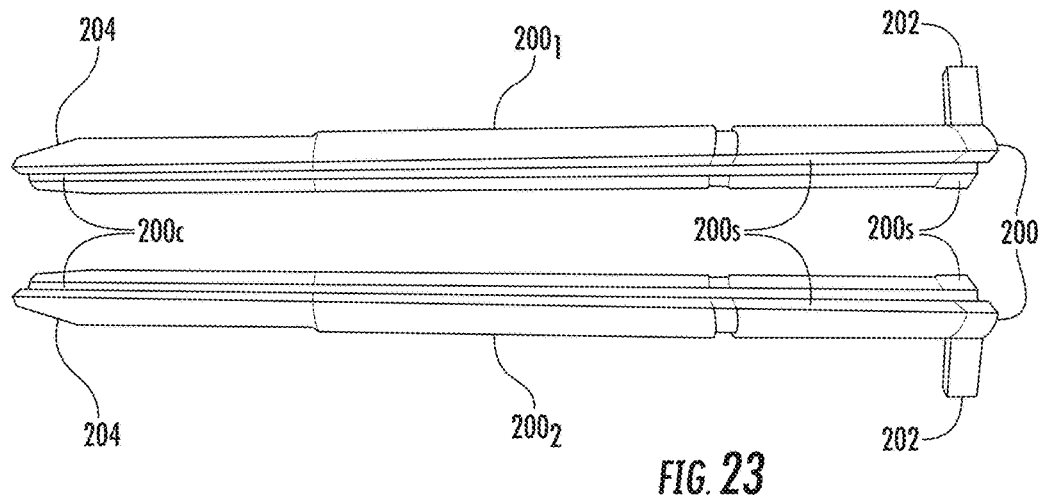
FIG. 23 is a side perspective view of an exemplary split body device guide according to embodiments of the present invention.

The device guide 200 may have a bore size (e.g., diameter) that is smaller by at least 50%, typically with a bore size that is between about 2-3 mm. The device guide 200 distal end 200b resides below the guide support distal end 1102b. The device guide 200 can have outwardly extending lugs 202 that engage a laterally extending slot 1103 in the device guide support 1102 to be releasably secured thereto. The lugs 202 can enter a longitudinally extending slot 1103l to a desired level or one or more traverse slots 1103t to reside at a proper position/height (FIG. 23). The lugs 202 cooperate with the slots 1103 (e.g., 1103l, 1103t, FIGS. 9, 23) to allow the device guide 200 to be inserted within the device guide support 1102. By rotating the device guide 200 such that the lugs 202 cooperate with the upper transverse slot 1103u, the device guide 200 can be positioned at a first or upper position. By inserting the device guide 200 further within the guide support 1102 and then rotating the device guide 200 such that the lugs 202 cooperate with the lower transverse slot 1103t, the device guide 200 can be securely held at a second or lower position, which is the position shown in FIG. 1.

The surgical device guide 200 can be configured as first and second cooperating, detachable elongate members $200_1$, $200_2$ (FIGS. 23 and 24, for example) that cooperate to define a longitudinally extending open channel 200c and that separate along longitudinally extending split lines 200s. The two members $200_1$, $200_2$ can face each other to define a cylindrical through channel 200c when the respective walls forming the split lines are abutting or in close proximity thereof. The two members $200_1$, $200_2$ can attach together or merely be held together or closely spaced apart by the guide support 1102, for example. The device guide 200 can have diametrically opposed split lines 200s. The split lines 200s are typically pre-formed, e.g., the device guide 200 is provided at a point of use (or in a kit) as two separate discrete components and/or as two components releasably attached together for use in the surgical system. The guide device 200 may also be preferentially scored or otherwise formed with a thinner wall segment relative to adjacent wall segments along a split line, so that two elongate cooperating members $200_1$, $200_2$ can be easily separated by a user during or before a surgical procedure.

As will be discussed further below, the device guide 200 can cooperate with upper and lower docks 400, 300, respectively (FIG. 2A, 2B, 5A, 5B) that may have respective dock inserts 401, 301 with first and second cooperating members $401_1$, $401_2$ (FIG. 7) and $301_1$, $301_2$ (FIG. 8) that define a through channel and have longitudinally extending split lines 401s, 301s (FIGS. 7, 8) for separation.

Figure 12:
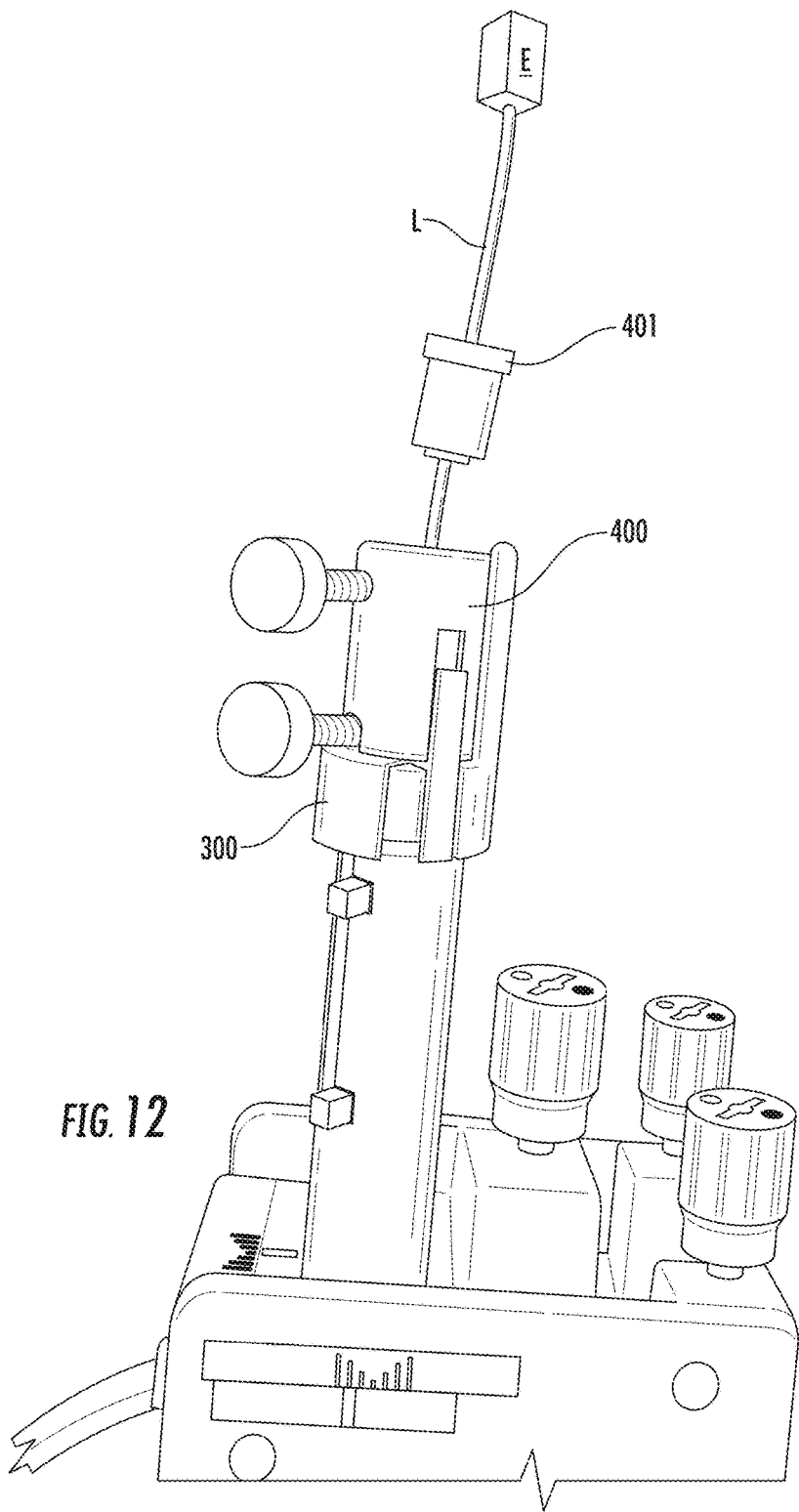

FIG. 12 illustrates an example of a lead assembly L with an integrated connector or "electronics package" E of connectors for the implantable electrodes (e.g., between 16-128 electrodes, typically about 64 electrodes) that has a size that is much greater than the flexible lead body which can interfere with the removal of the trajectory frame 100 and cooperating components, after the distal end of the lead is locked into position in a patient, such as with a STIMLOCK.

Thus, as shown in FIG. 3, a lock member 400, dock member 300, and removable guide support cap 500, can be provided with through-channels or bores 300b, 400b, 500b, with larger sizes, typically between about 7-9 mm, as shown about 7.3 mm, to be able to slide over the electronics package E (FIG. 12).

Figure 20:
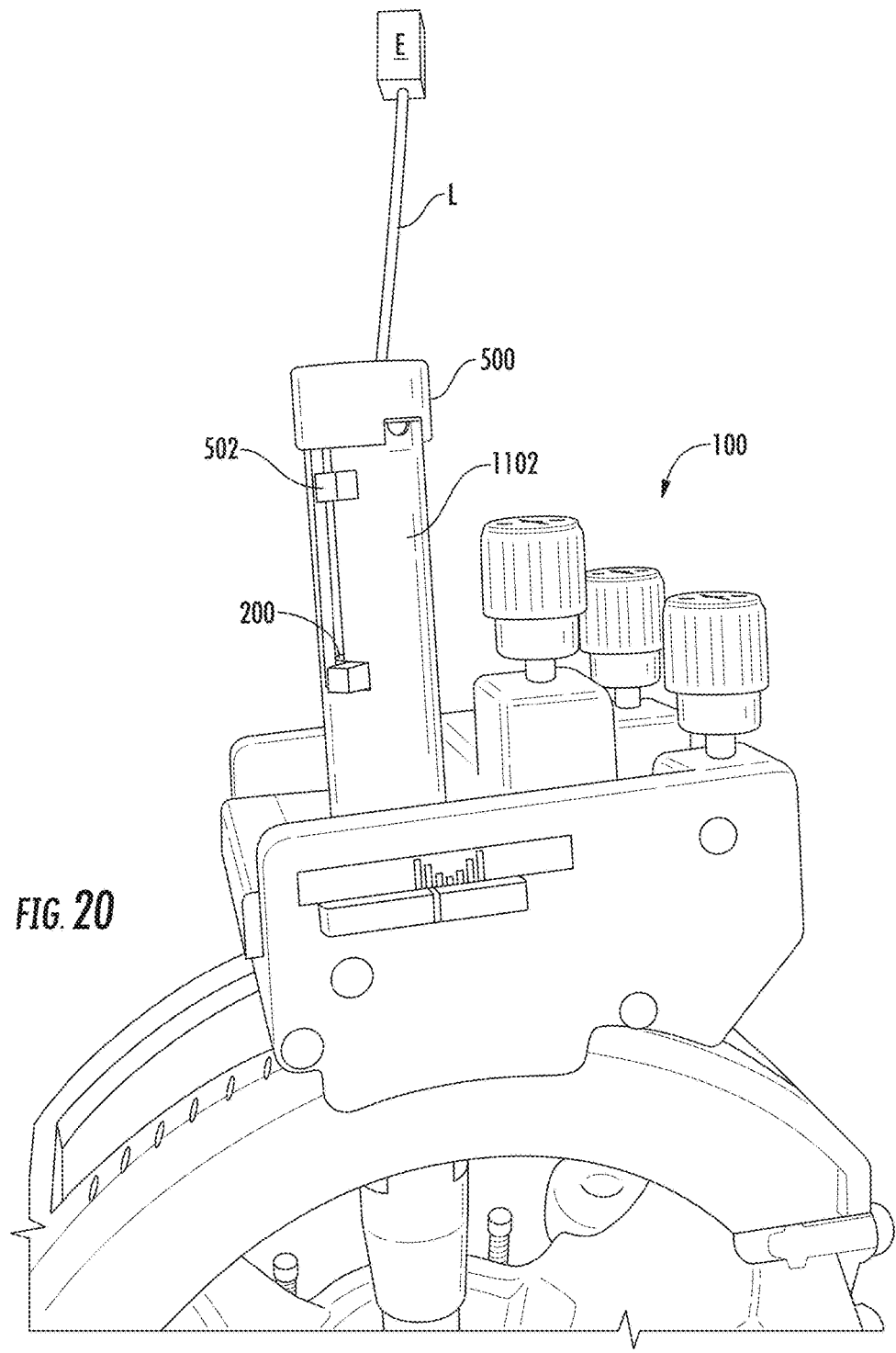

The cap 500 can optionally have lugs 502 that engage a slot or slots 1103 of the upper end portion of the guide support 1102 (FIG. 20).

FIG. 1 illustrates the dock member 300 attached to the lock member above the cap 500, with each held by the guide support 1102.

Figure 2A:
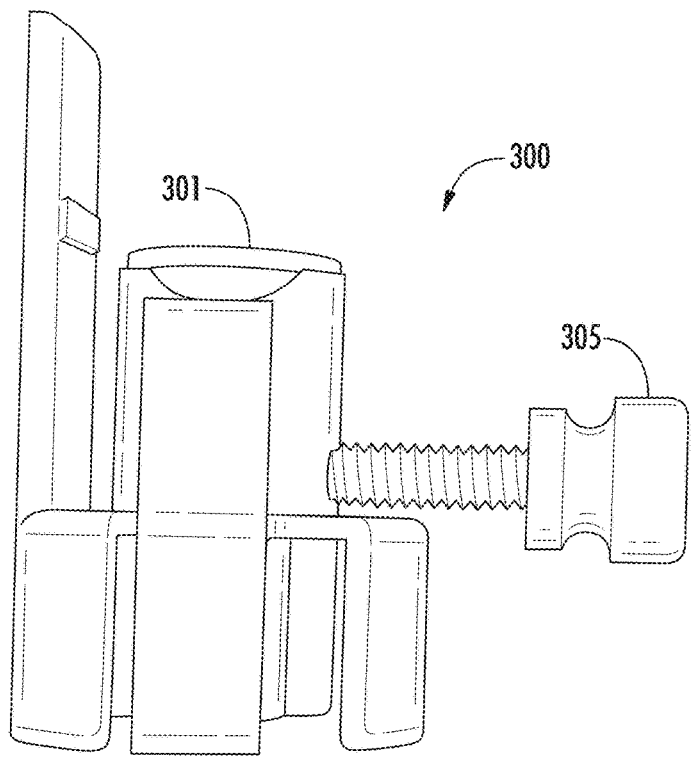
FIG. 2A is an enlarged side perspective view of a dock member with a clock insert according to embodiments of the present invention.
Figure 2B:
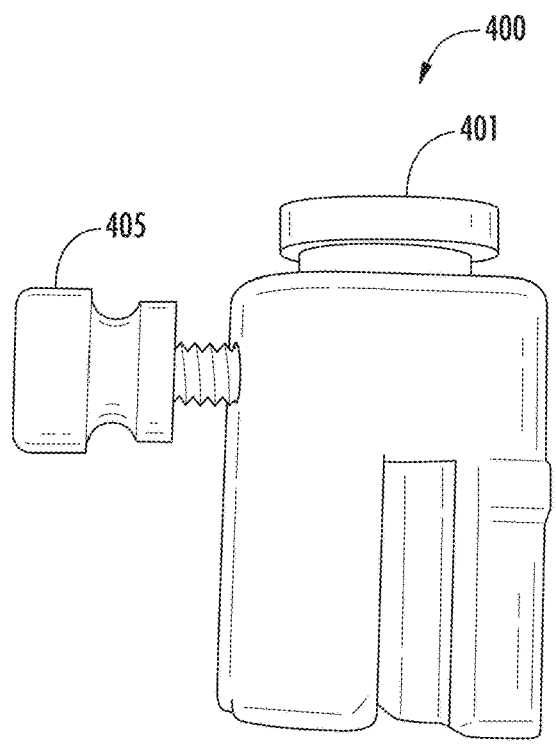
FIG. 2B is an enlarged side perspective view of a lock member with a lock insert according to embodiments of the present invention.

FIGS. 2A and 2B illustrate that the dock member 300 and lock member 400 can each include inserts 301, 401, respectively, and at least one fixation member, such as a screw or thumb drive 305, 405. The dock member and lock member 300, 400, respectively can each include an aperture 300a (FIG. 8), 400a (FIG. 7) through a sidewall thereof that receives the fixation member. The inserts 301, 401 can also include an aligned aperture 301a (FIG. 18) that allows the fixation member to extend therethrough to contact a device in the bore 300b, 400b.

Figure 5A:
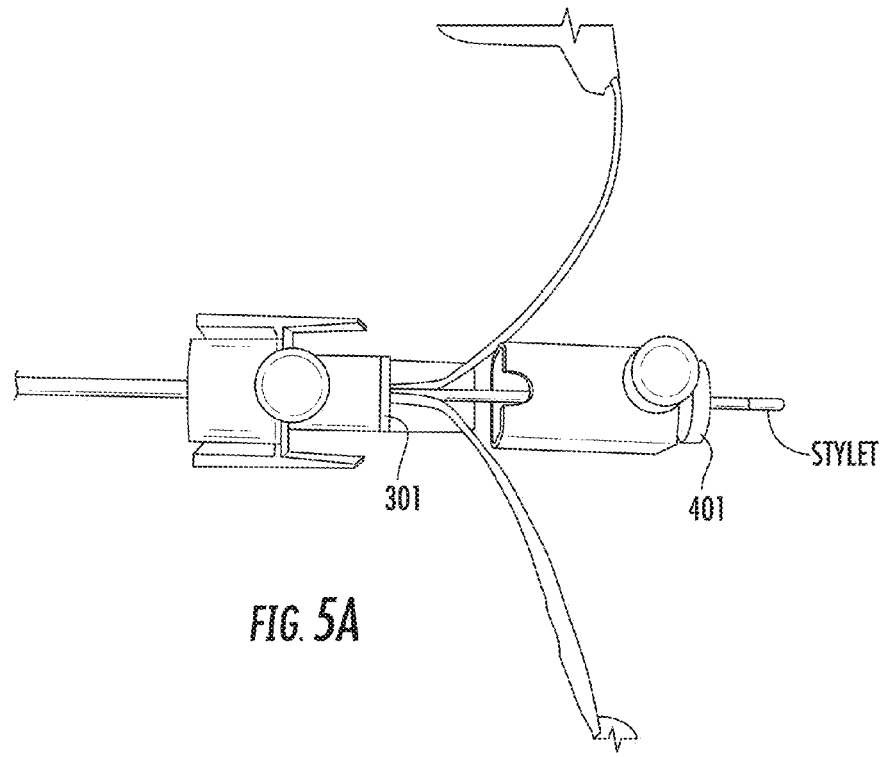
FIGS. 5A and 5B are enlarged side perspective views of a dock member and insert aligned with a lock member and insert with the stylet extending therethrough and upper ends of the sheath extending out between the lock and dock members according to embodiments of the present invention.
Figure 5B:
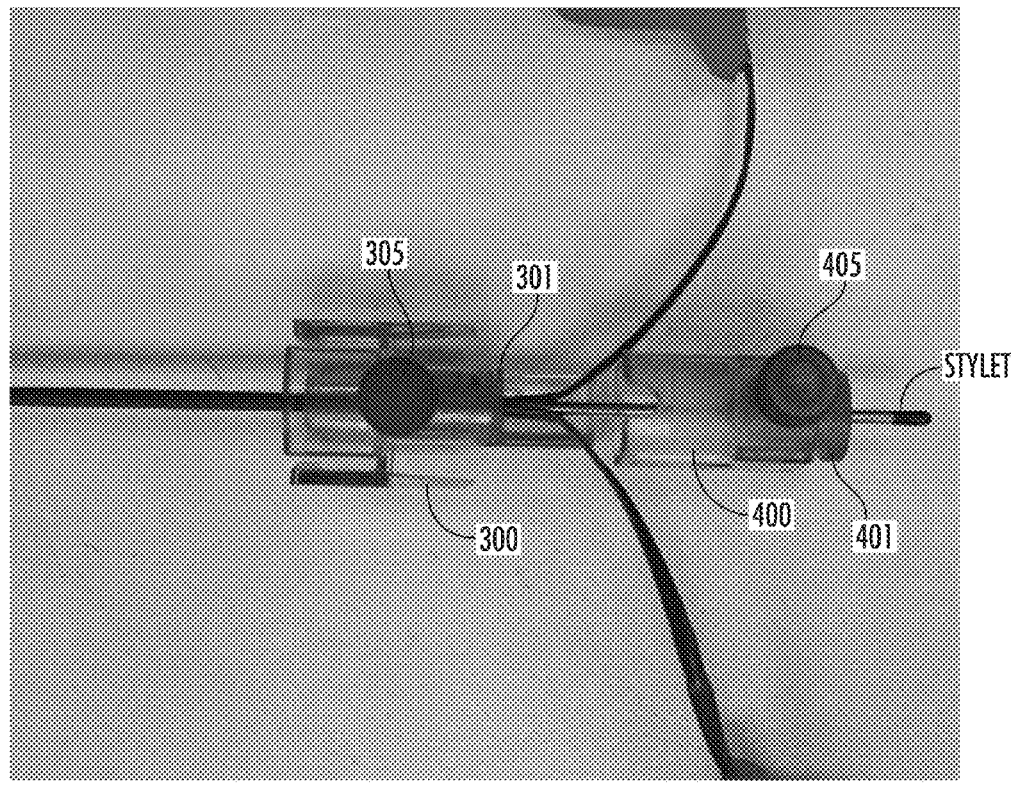
Figure 6A:
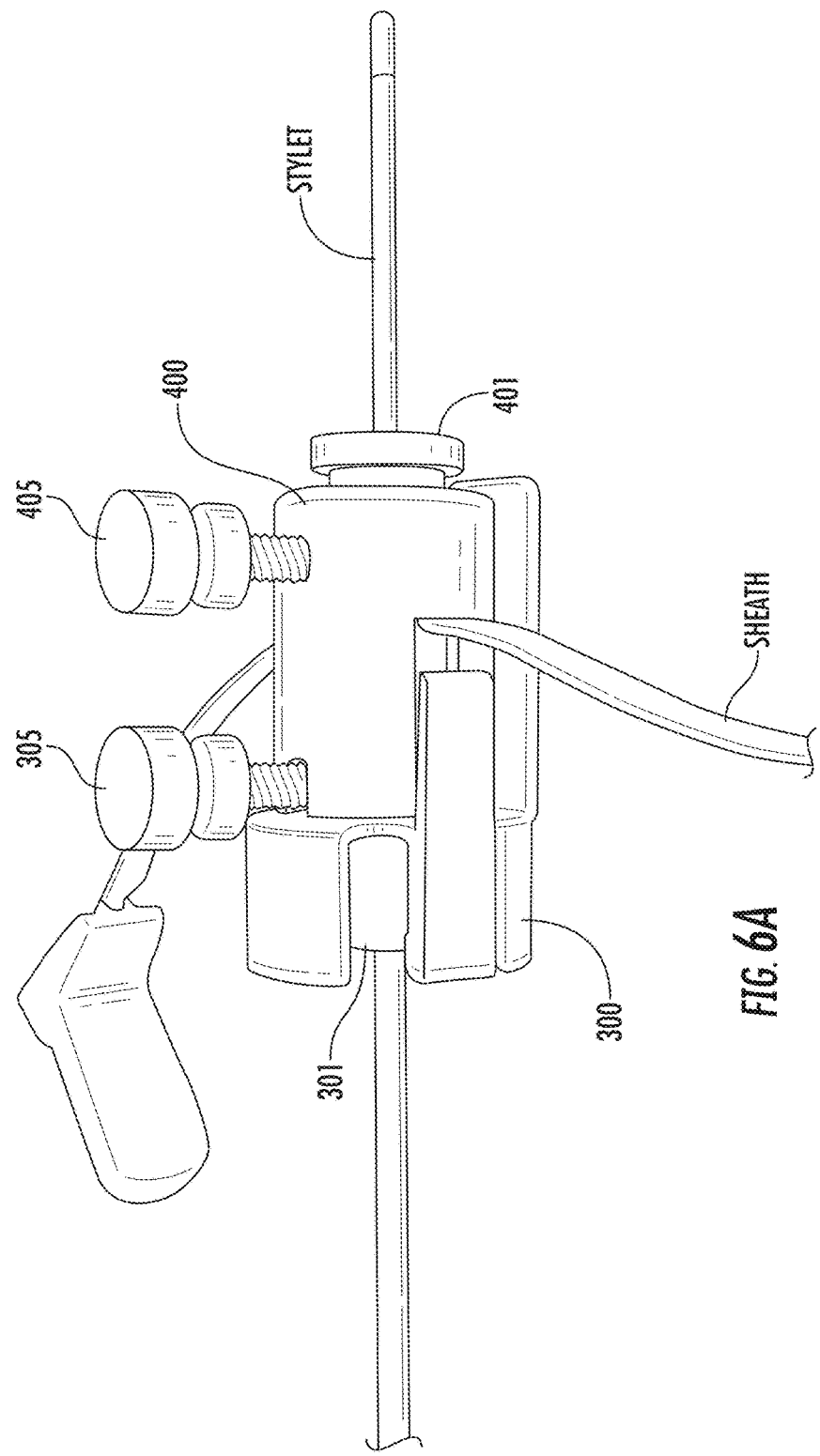
FIGS. 6A and 6B are enlarged views of the lock and dock components shown in FIG. 5A attached together according to embodiments of the present invention.
Figure 6B:
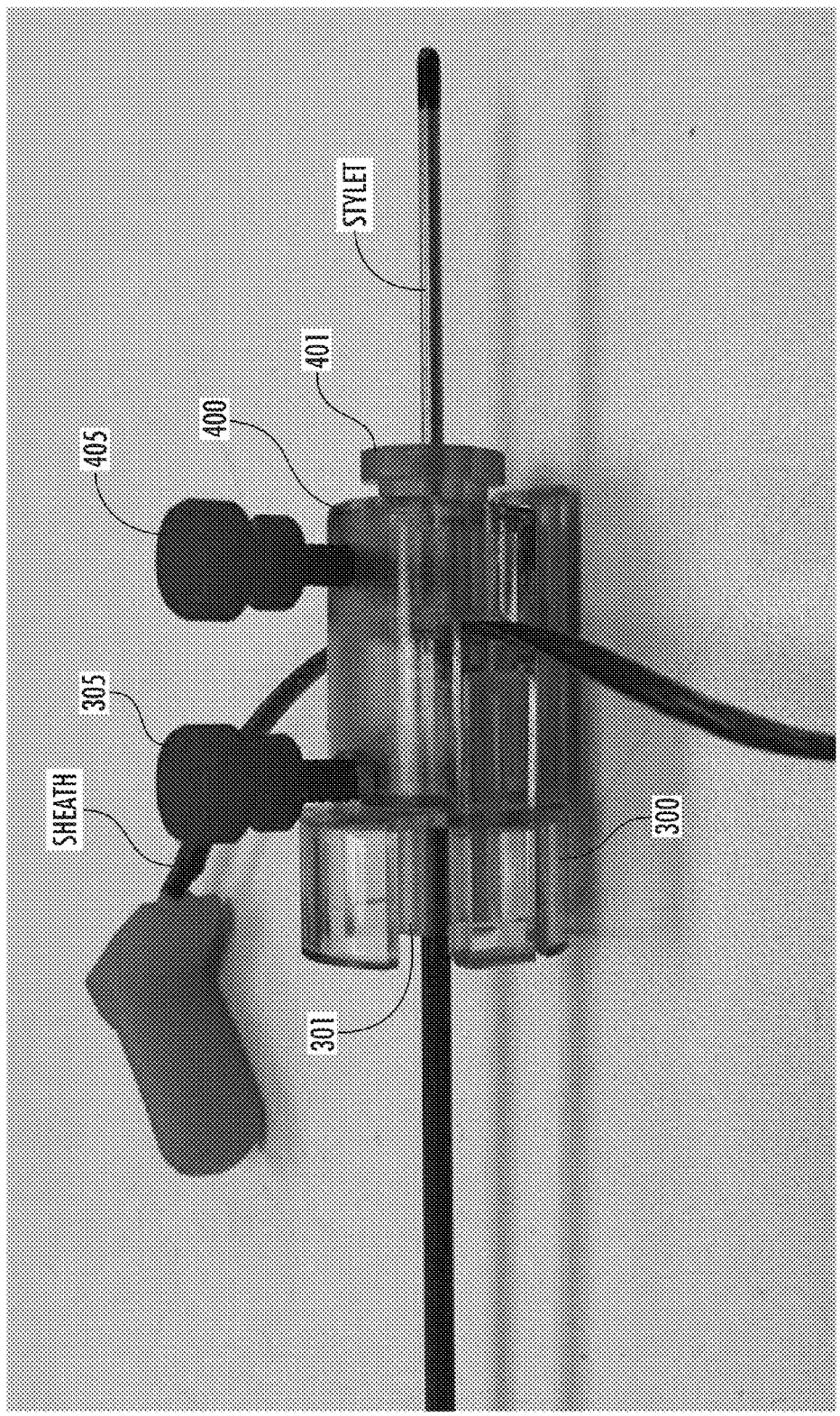

FIGS. 4, 5A/5B and 6A/6B illustrate the dock member 300 and lock member 400 without the trajectory frame 100 illustrating an optional assembly protocol to attach the dock member 300 and lock member 400 to a sheath with a stylet extending through the aligned bores 300b, 400b. The fixation members 305, 405 can be tightened to against the stylet.

Figure 7:
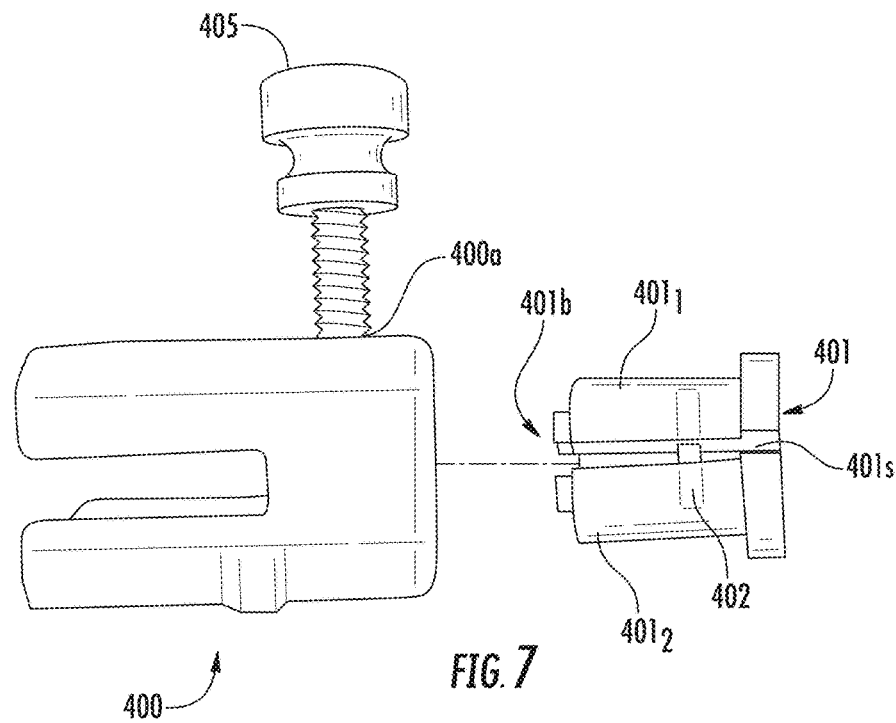
FIG. 7 is an exploded view of the lock member and lock insert shown in FIG. 2B according to embodiments of the present invention.

FIG. 7 shows an exploded view of the lock member 400 with the insert 401. The lock member insert 401 can have a split body with first and second matable segments $401_1$, $401_2$ that can be releasably secured together to form a through bore or channel 401b that is smaller than that of the lock member bore 400b, typically at least 50% smaller in cross-sectional area, e.g., diameter, such as having a diameter that is between 2-4 mm, for example. The segments $401_1$, $401_2$ can be elongate and attach to define a cylindrical bore or channel. The segments $401_1$, $401_2$ can be semi-circular and/or with an arcuate, concave wall. The split lines 401s can be diametrically opposed and extend in a straight line. The two segments $401_1$, $401_2$ can be retained with a laterally extending locating or retaining pin or key 402 that allows them to be slidably removed from the lock member body as a unit (FIG. 12). However, the split lines 401s may be "zig-zag" or other shape and may be self-retaining but releasably secured together and/or other retention configurations or members may be used.

Figure 8:
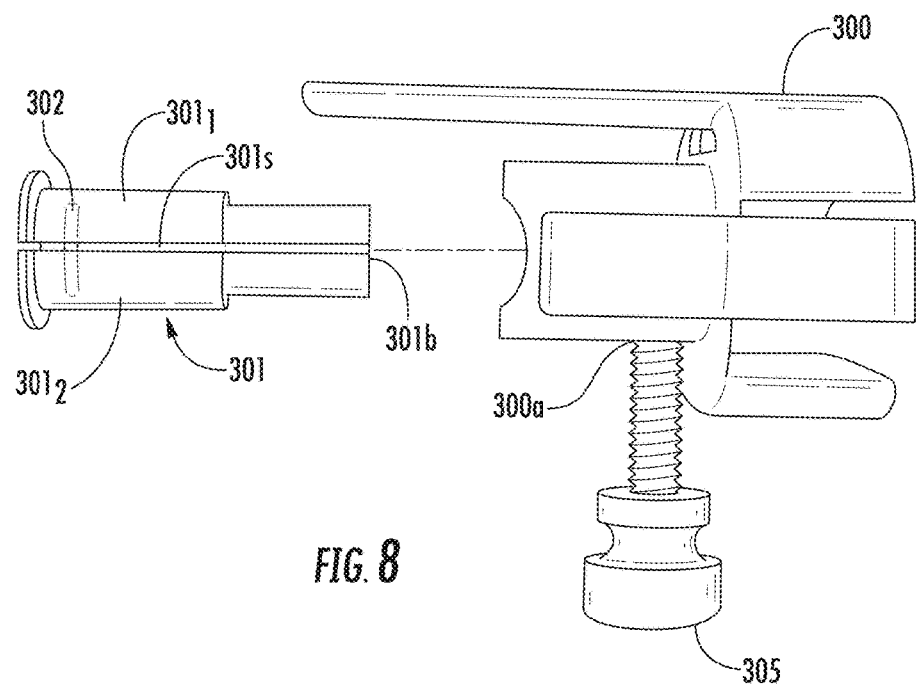
FIG. 8 is an exploded view of the dock member and dock insert shown in FIG. 2A according to embodiments of the present invention.

FIG. 8 shows an exploded view of the dock member 300 with the insert 301. The dock member insert 301 can also have a split body with first and second matable segments $301_1$, $301_2$ that can be releasably secured together to form a through bore or channel 301b that is smaller than that of the lock member bore 300b, typically at least 50% smaller in cross-sectional area, e.g., diameter, such as having a diameter that is between 2-4 mm, for example. The segments $301_1$, $301_2$ can be elongate and attach to define a cylindrical bore or channel. The segments $301_1$, $301_2$ can be semi-circular and/or with an arcuate, concave wall. The split lines 301s can be diametrically opposed and extend in a straight line. The two segments $301_1$, $301_2$ can be retained with a laterally extending locating or retaining pin or key 302 that allows them to be slidably removed from the lock member body as a unit (FIG. 16). However, the split lines 301s may be "zig-zag" or other shape and may be self-retaining but releasably secured together and/or other retention configurations or members may be used.

Although not shown, it is also contemplated that instead of or additionally with the inserts 301, 401, the dock and lock members 300, 400 can be configured with split lines with matable first and second segments to be able to be releasably secured together. For this embodiment, no inserts may be required or the inserts 301 and 401 may be used and each of the inserts 301, 401 and lock and dock members 400, 300 can be configured to have separable longitudinally extending components that form the bore 400b, 300b (FIG. 3).

Figure 9:
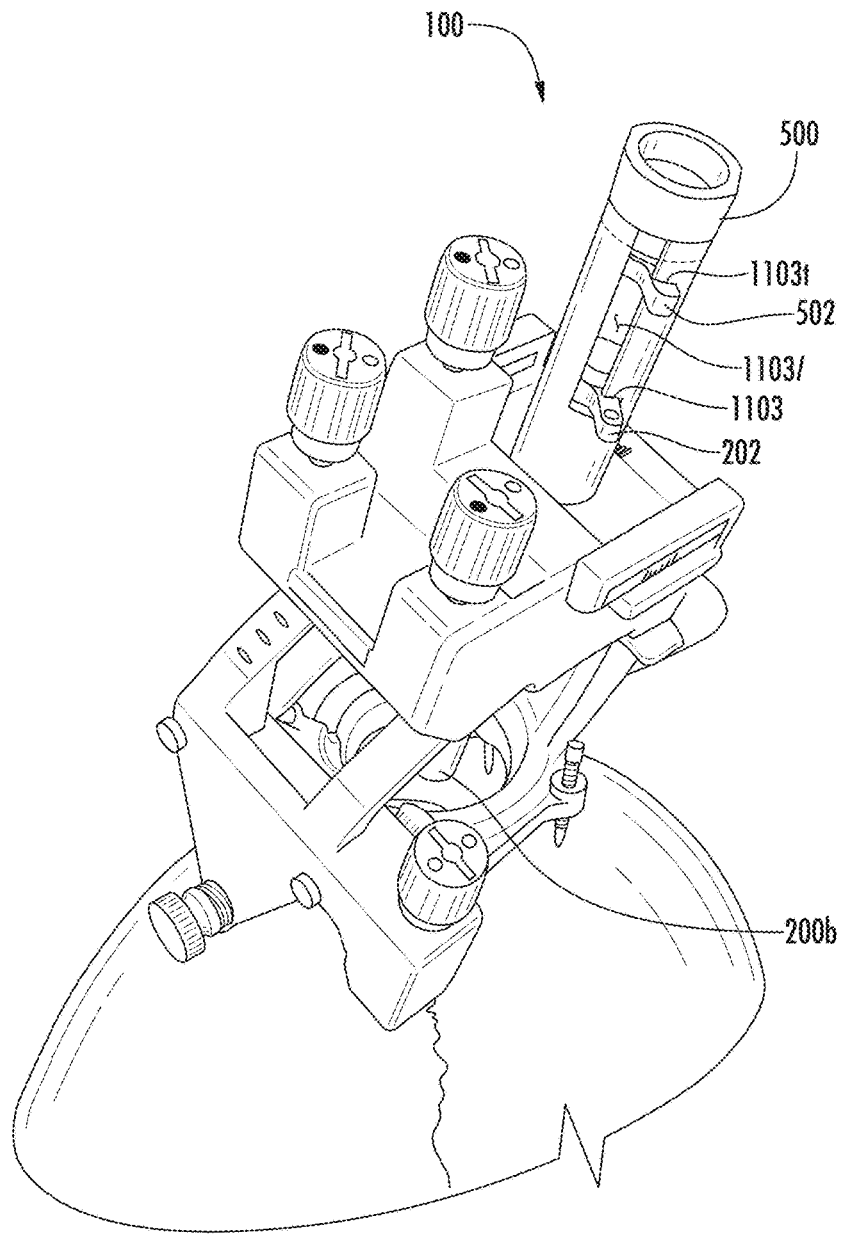
FIG. 9 is a side perspective view of the trajectory frame assembly with the removable device guide support cap as the upper component with the dock and lock members removed according to embodiments of the present invention.

FIG. 9 illustrates that trajectory frame 100 with the device guide support 1102 and the cap 500 residing on an upper surface of the guide support with lugs 502 secured in a transverse slot 1103t.

Figure 10A:
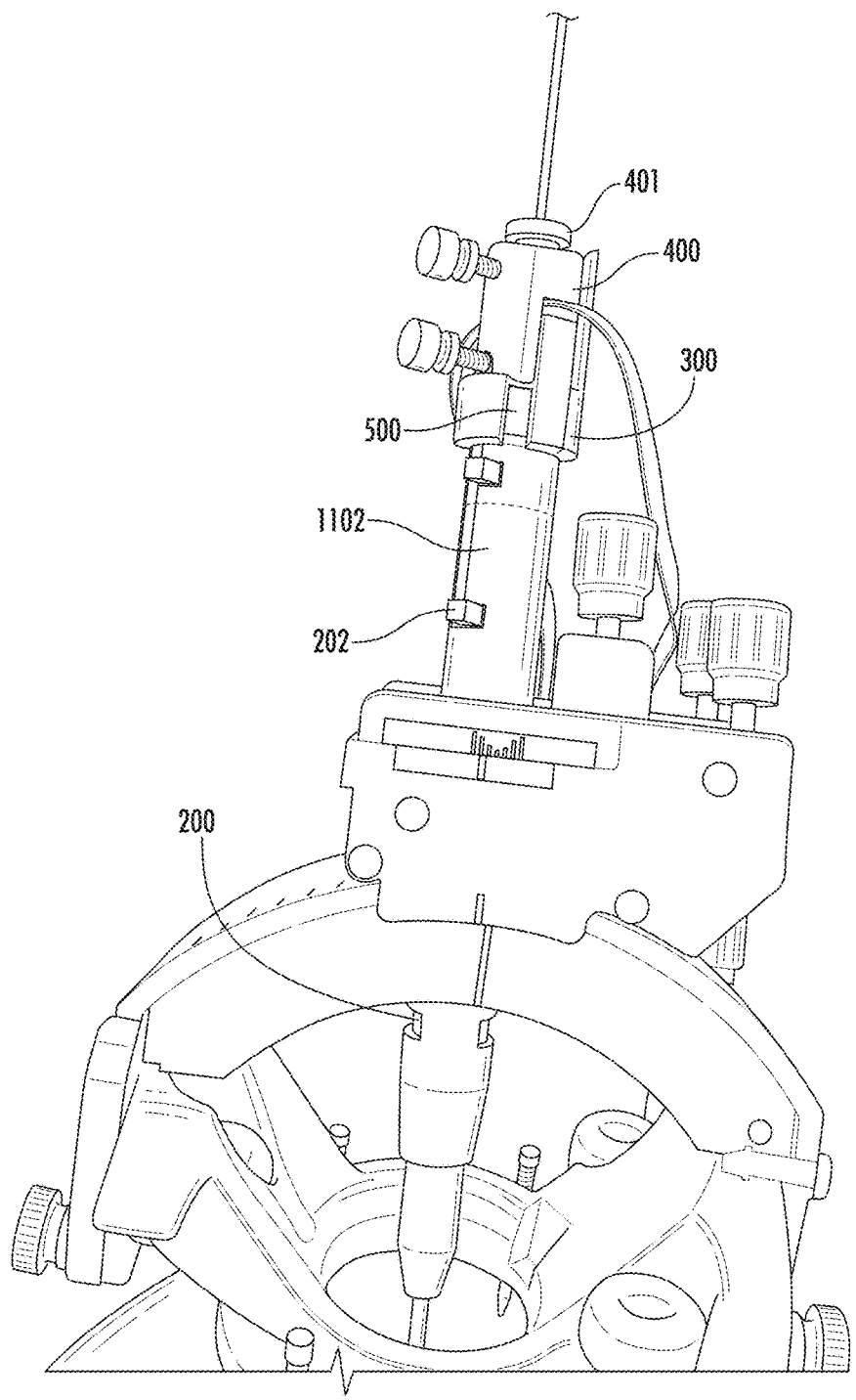
FIGS. 10A and 10B are side perspective views of the assembly shown in FIG. 1 with a stylet and sheath in position according to embodiments of the present invention.
Figure 10B:
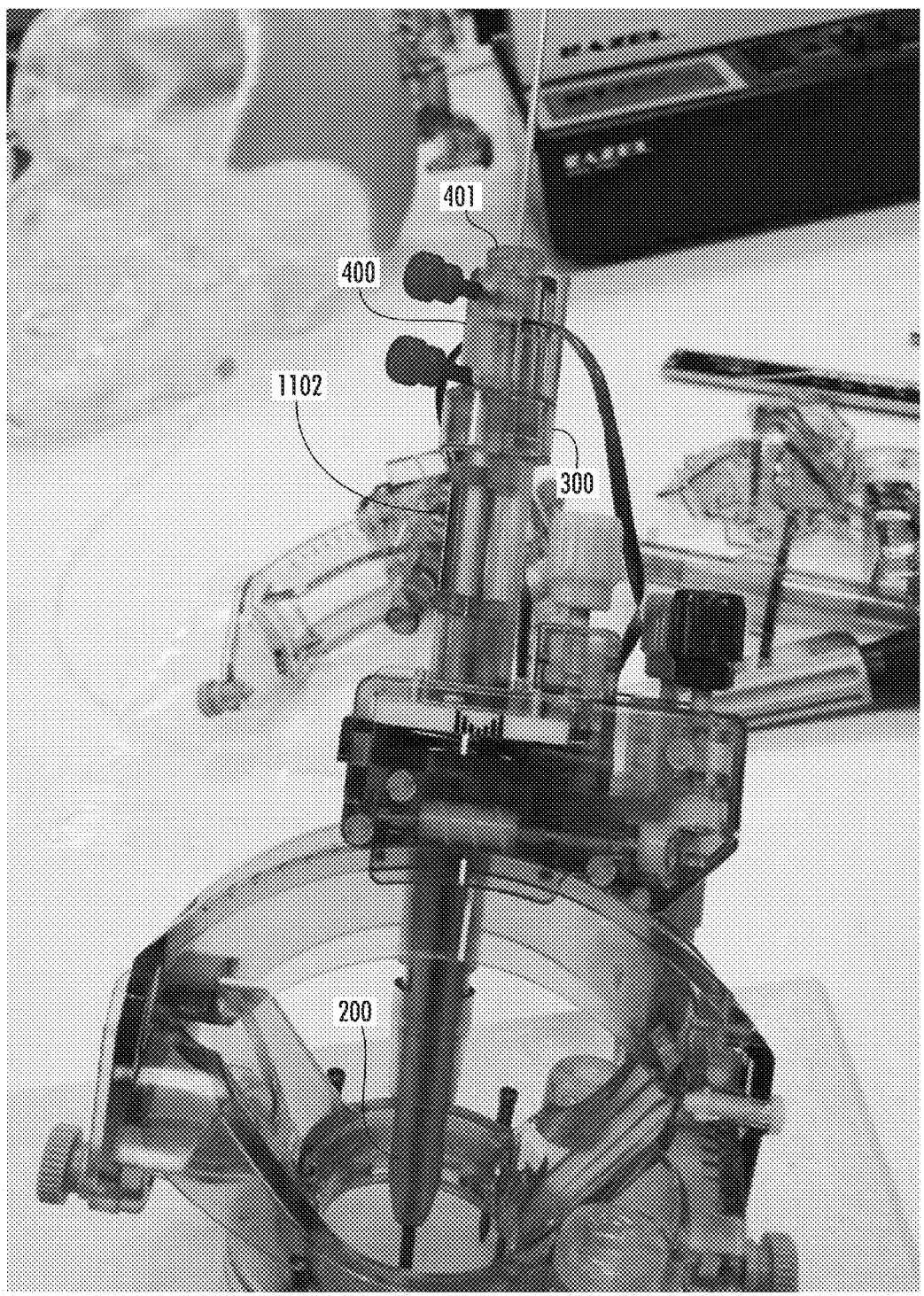

FIGS. 10A and 10B illustrate the dock member, lock member and cap 300, 400, 500, respectively in the trajectory frame 100 with the device guide holding the stylet and sheath.

Figure 11:
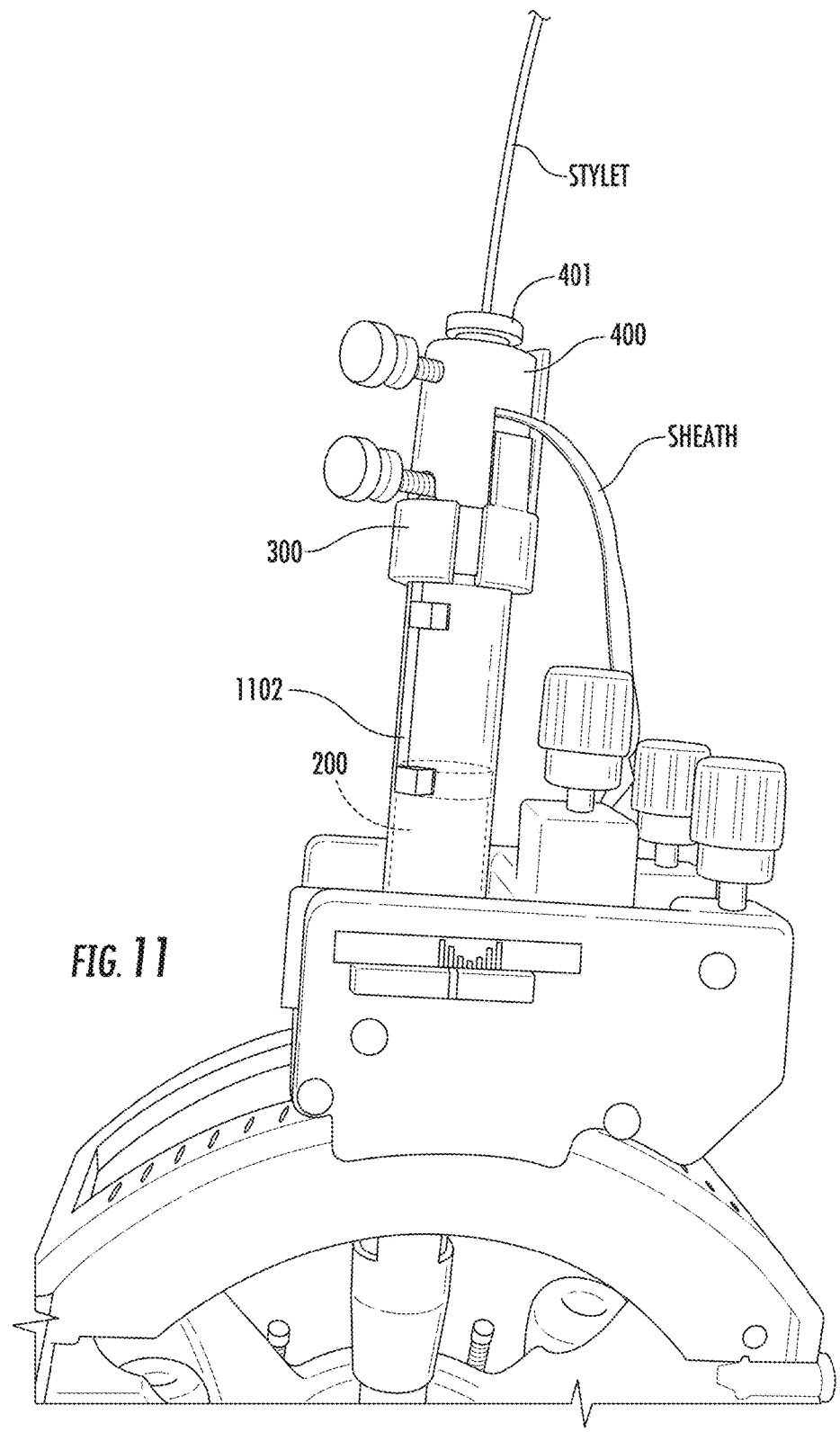
FIG. 11 is a side perspective view of a simulated lead configuration being inserted through the dock and lock into the sheath according to embodiments of the present invention.

FIG. 11 shows the stylet removed and the lead inserted through the lock member 400 and the dock member 300 and into the sheath through the device guide 200. Although not shown, once the lead L is in position, the peel away sheath is removed and a STIMLOCK or other lock can be attached to a patient to hold the lead to the skull. As is well known, the sheath extends to a desired target and is left in place to act as a delivery cannula for the implantable lead which is then removed (the sheath is pulled outward), once the lead is at the target. The trajectory frame disassembly procedure can then be carried out.

Figure 14A:
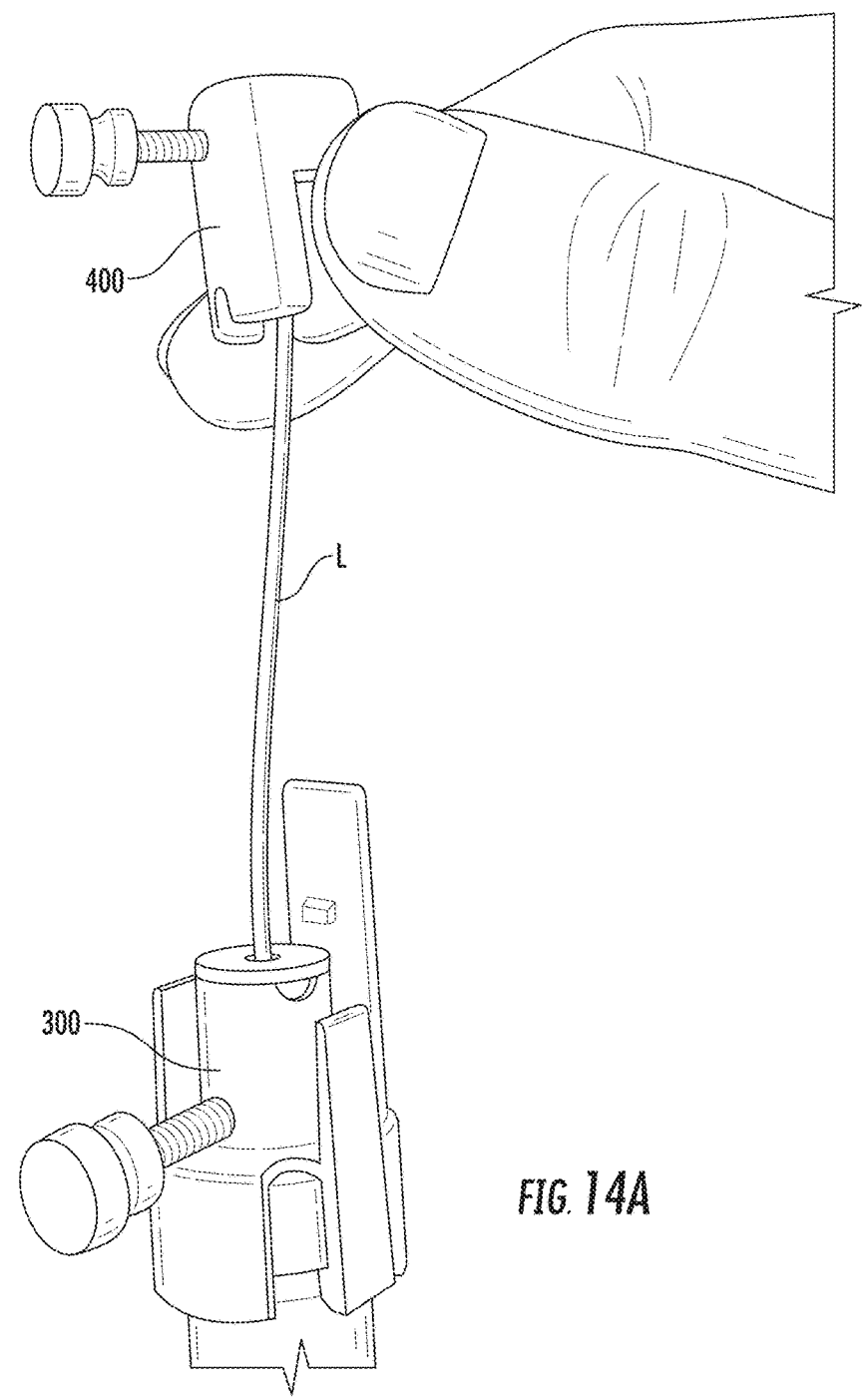
Figure 14B:
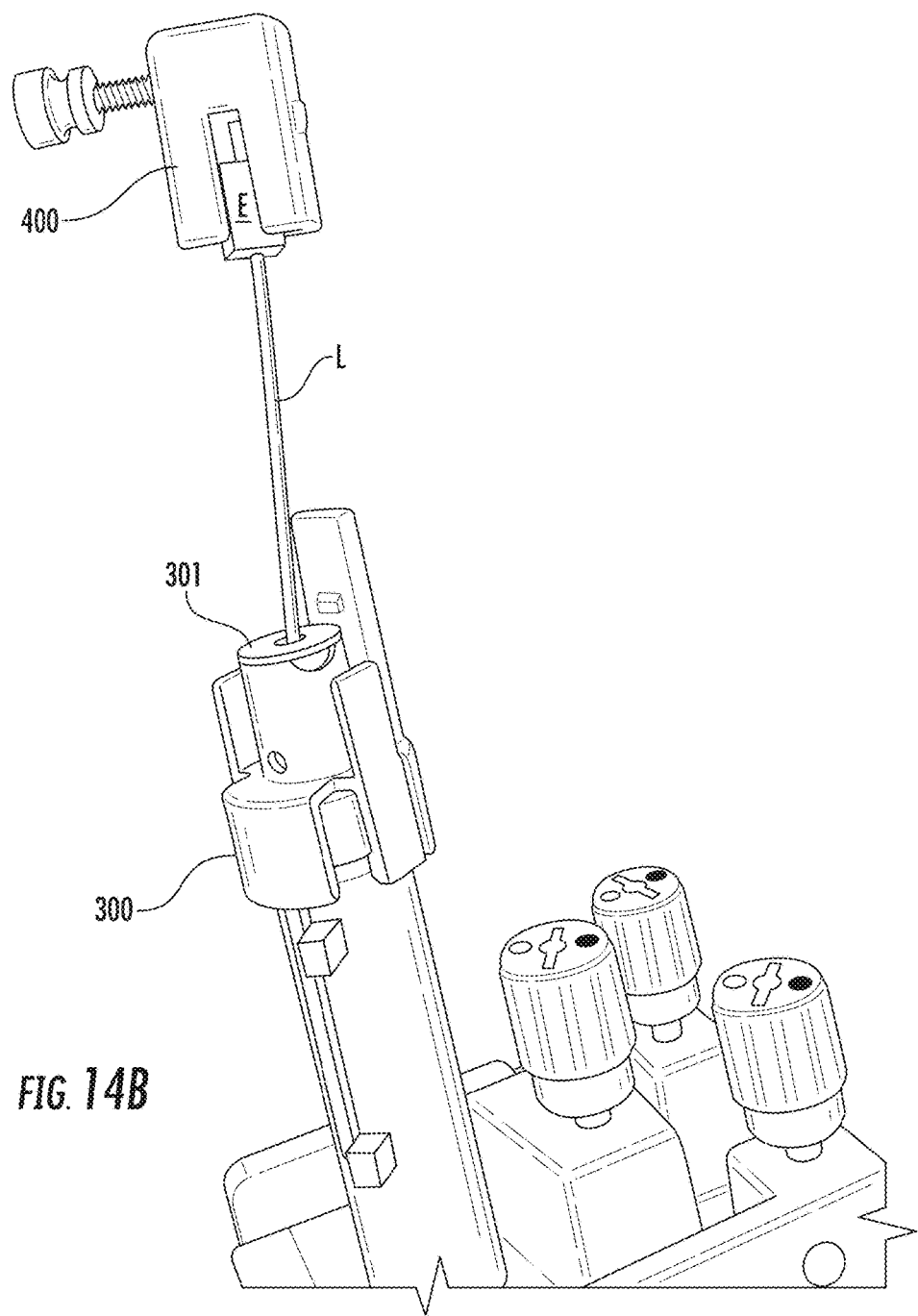
Figure 15:
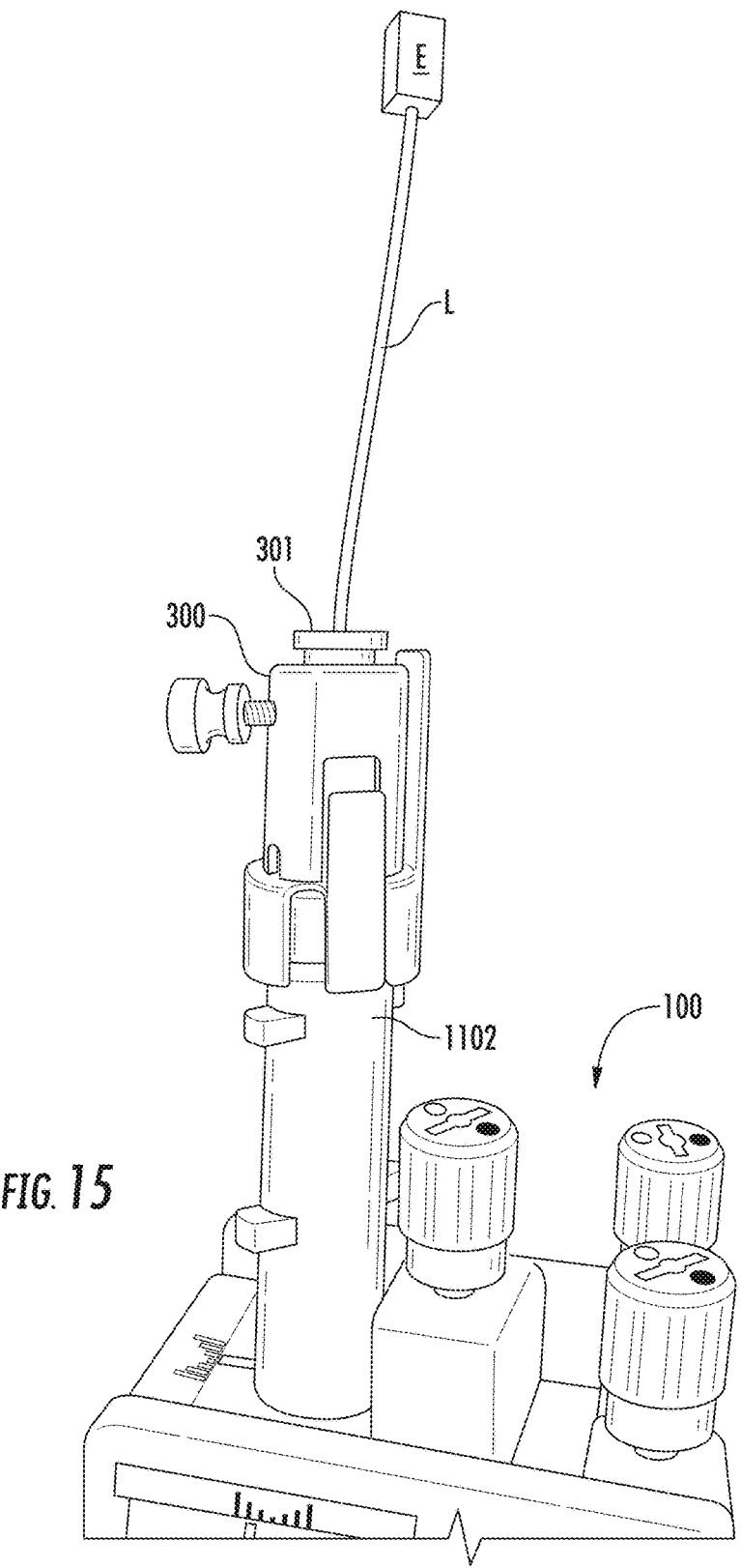
Figure 17A:
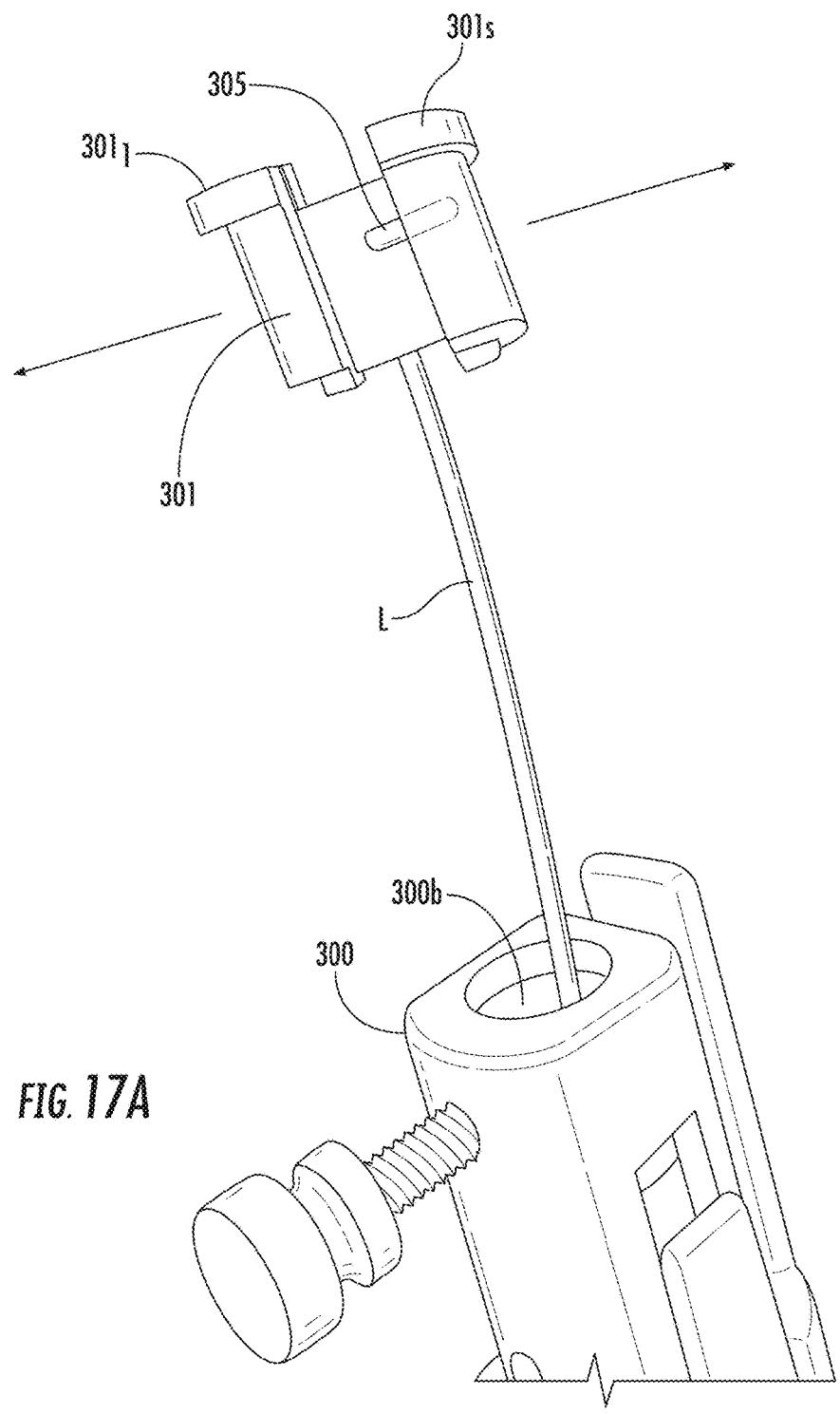
FIG. 17A is a line drawing of a corresponding photograph shown in FIG. 17B.
Figure 17B:
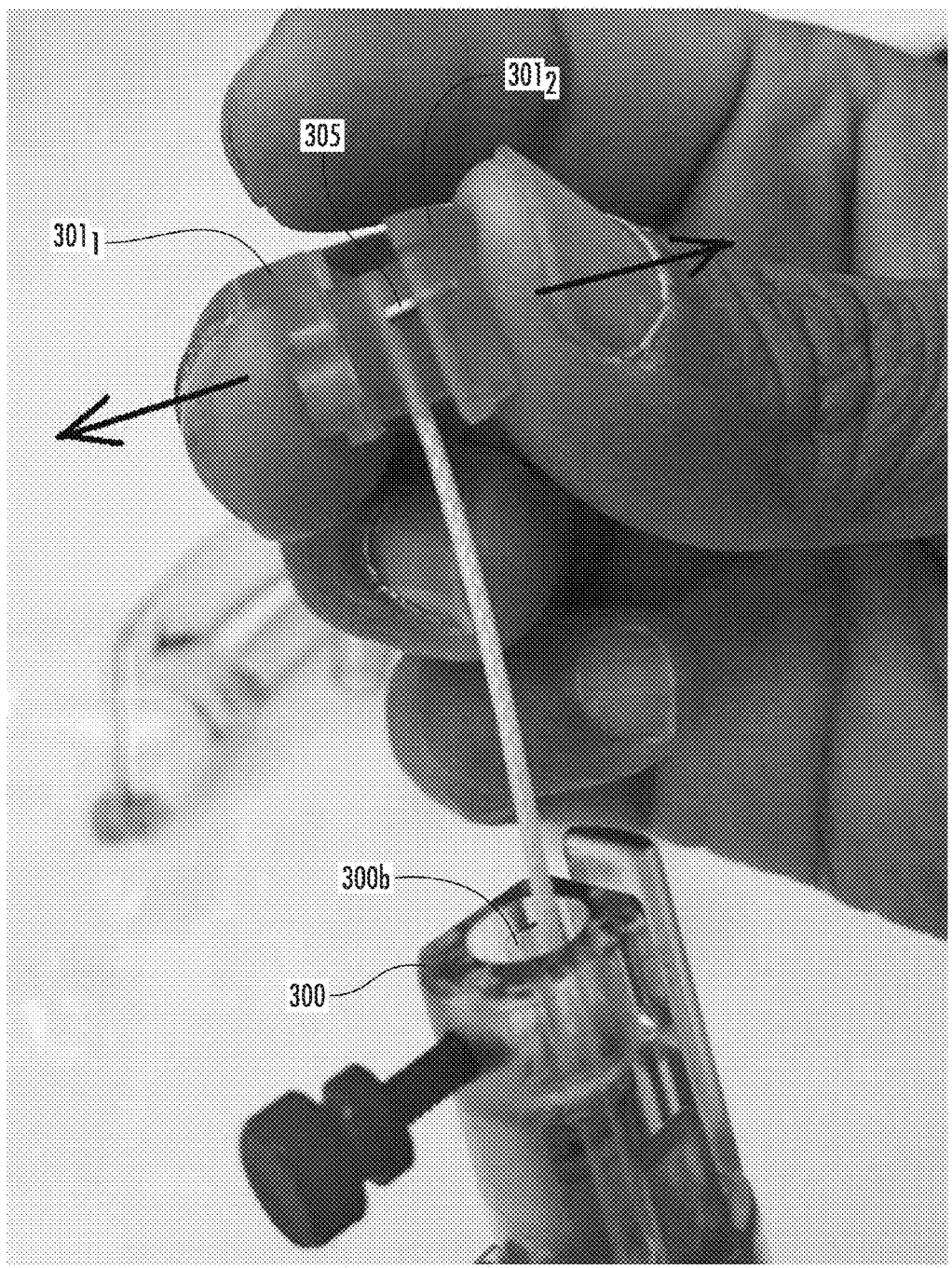
Figure 18:
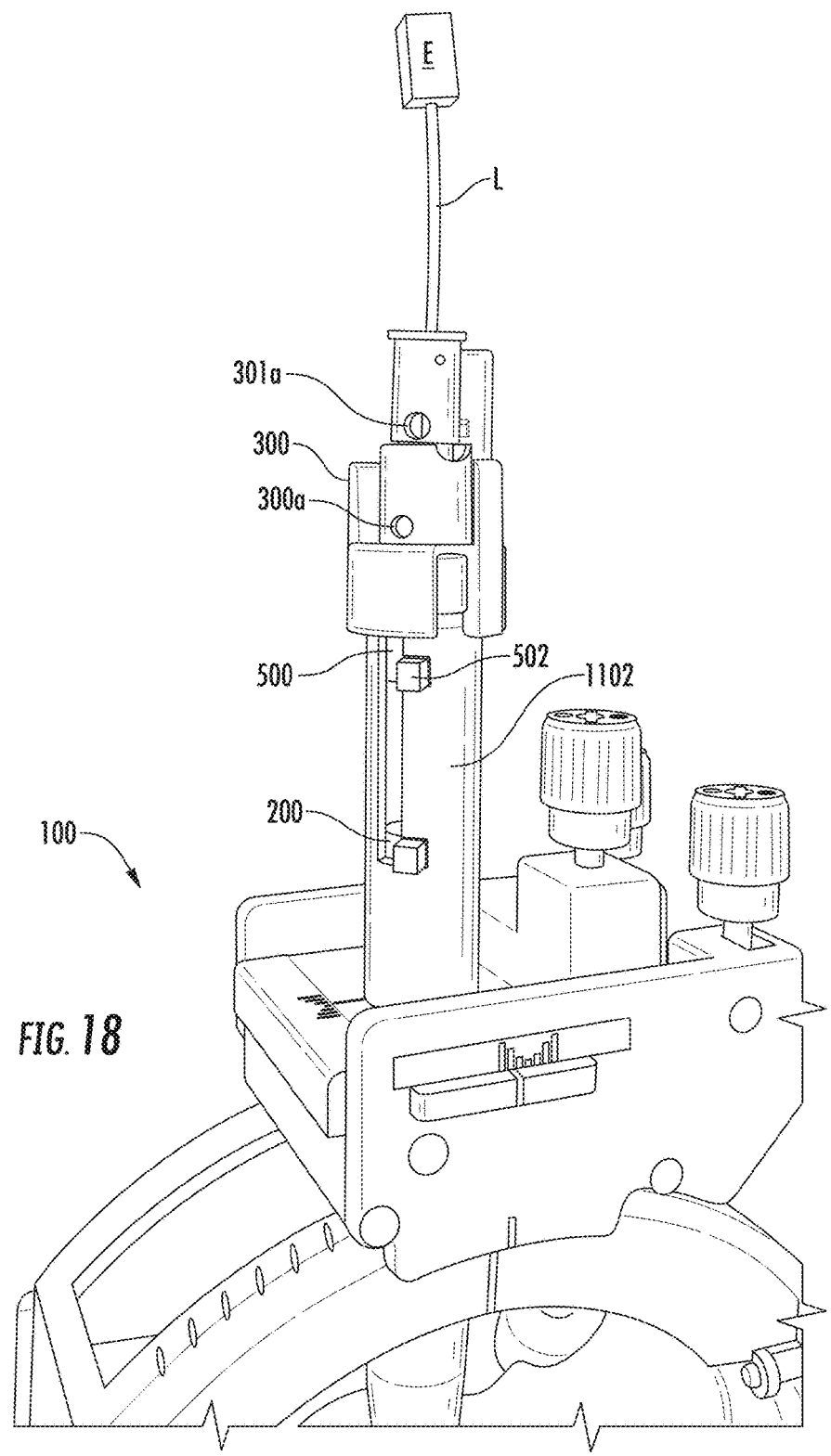
Figure 19:
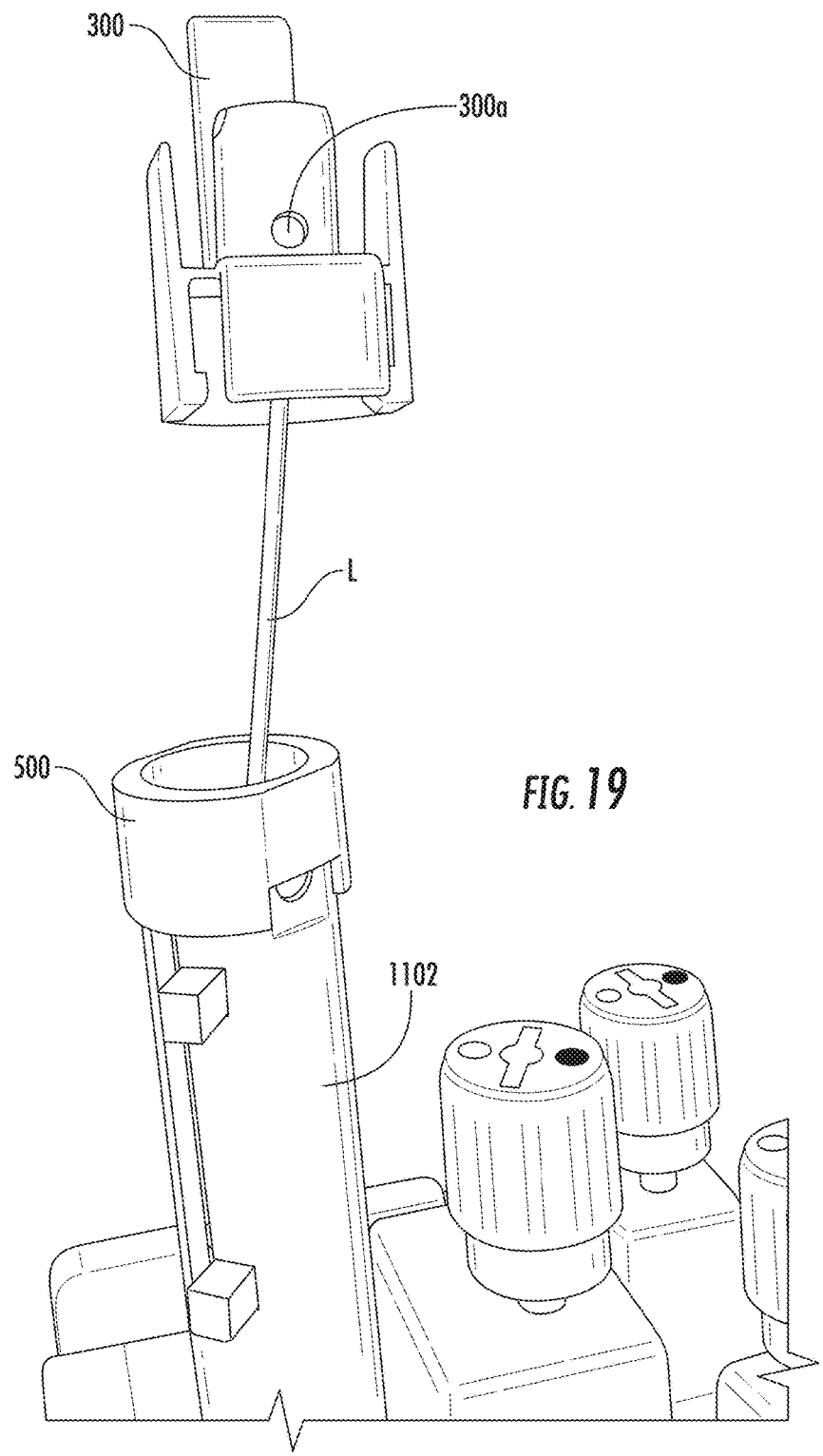

FIG. 12 shows the lock member insert 401 slide out of the lock member 400 over the exposed part of the simulated lead L. For this and subsequent images, the sheath is not really in the device at this point. FIG. 13 shows the lock member insert 401 being separated into two pieces beneath the electronics package E. FIGS. 14A and 14B illustrate the lock member being slid over the end of the lead. FIG. 15 illustrates that the dock member 300 and dock member insert 301 are still on the support 1102. FIG. 16 shows the insert 301 being slid up toward the end of the exposed lead. FIGS. 17A and 17B show the dock member insert 301 being transversely separated into two components $301_1$, $301_2$. FIG. 18 illustrates the insert 301 as it is being slide out of the dock member 300 with fixation apertures 300a, 301a. FIG. 19 illustrates the dock member 300 being slid over the end of the exposed lead. FIG. 20 illustrates the cap 500 under the exposed end of the lead L with the other dock and lock members removed.

Figure 21:
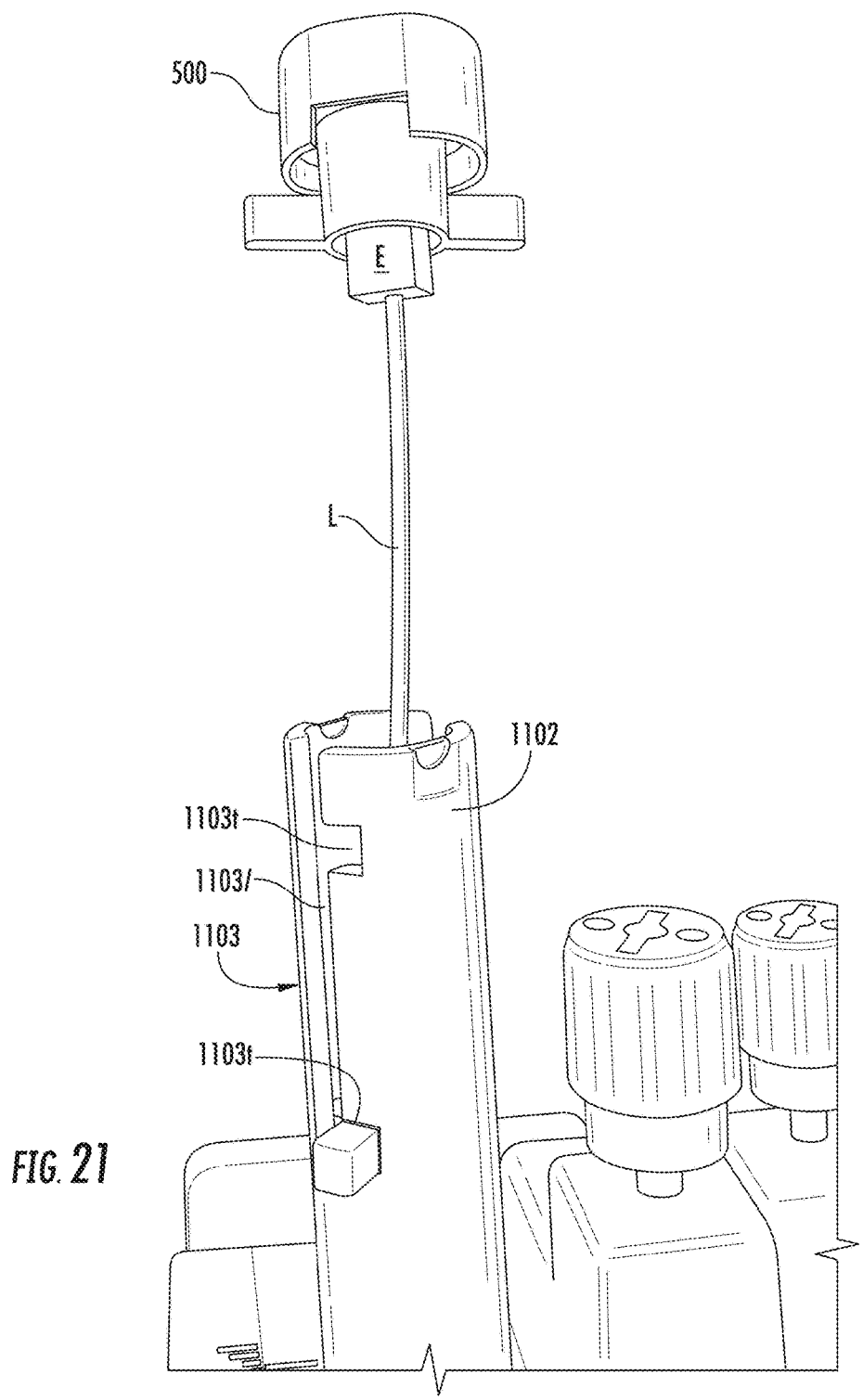

FIG. 21 illustrates that the cap 500 can also be slid over the exposed end of the lead (e.g., over the electronics package E). Although not shown, the cap may also be configured to be separated similar to the inserts 301, 401 discussed above.

Figure 22:
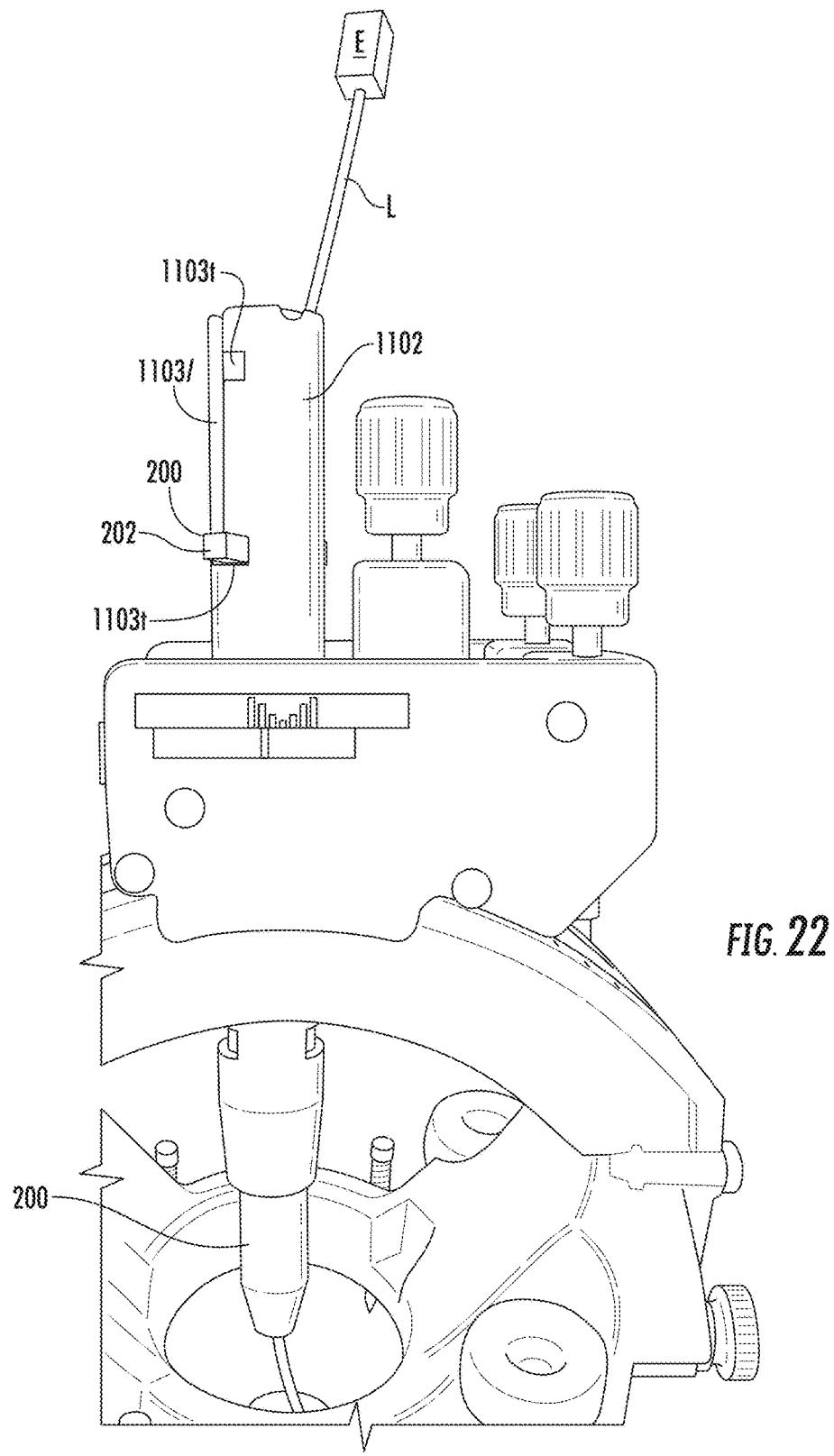

FIG. 22 illustrates the device guide 200 in the device guide support 1102 with lugs 202 engaged with a slot 1103t. The lugs are rotated and the device guide 200 can be pulled upward out of the support 1102.

As shown in FIG. 23, the device guide 200 can have a rigid split body and/or be configured to have first and second elongate segments $200_1$, $200_2$ that can be held in the guide support 102 to form a cylindrical channel 200c that extends therethrough. The device guide 200 may have a tapered distal end 204. The device guide 200 can have straight, diametrically opposed split lines 200s. The outer walls can be concave and encase a small diameter channel when abutting edges are held together.

The two segments $200_1$, $200_2$ can be withdrawn together as a unit and pulled apart above the guide support. In other embodiments, one segment can be slidably removed before the other.

Figure 24:
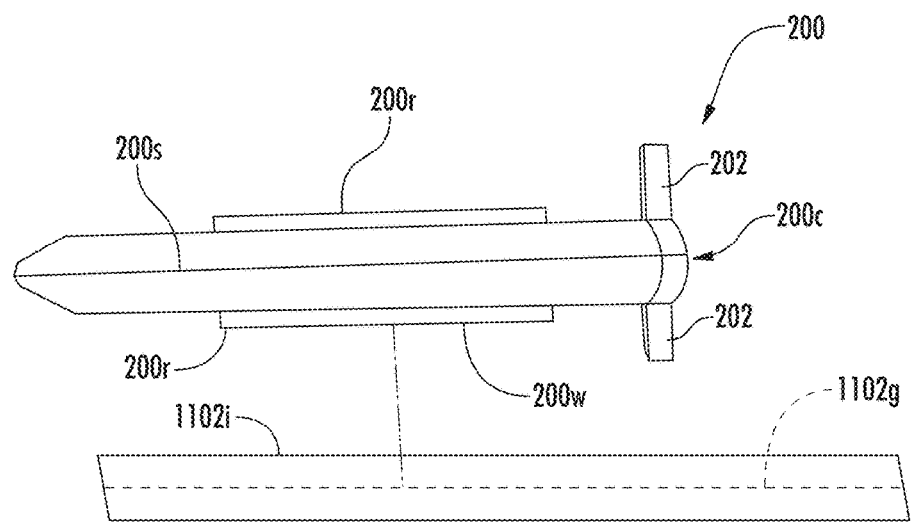
FIG. 24 is a schematic illustration of another exemplary split body device guide according to embodiments of the present invention.

In some embodiments, as shown schematically by FIG. 24, the walls 200w of the two segments $200_1$, $200_2$ can have an outersurface that can be configured to slidably engage rails or grooves of an inner wall 11021 of the device guide support 1102 to hold the two segments in cooperating alignment in the device 1102 and allow them to be separated when removed but configured so that the walls of the two segments at the tapered lower end remain in contact to define the guide channel inside the support device 1102. As shown, the device guide 200 includes rails or fins 200r that engage a groove or channel 1102g in the inner wall 1102i of the support 1102, (e.g., a tongue and groove configuration) although the opposing or other releasably locking engagement can be used.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical device guide in combination with a device guide support, the surgical device guide comprising first and second elongate semi-circular members that cooperate to define a longitudinally extending open channel and that separate along longitudinally extending split lines into discrete first and second elongate semicircular members, and wherein the first and second elongate semi-circular members are rigid and have a fixed common shape both when attached and when separated, wherein the surgical device guide is held by the device guide support, wherein the device guide support has a length and is configured to be secured to a platform of a trajectory frame assembly, wherein the device guide support comprises opposite proximal and distal end portions, wherein the device guide support comprises a bore therethrough that extends from the proximal end portion to the distal end portion, and wherein the surgical device guide has a length with a lower end portion extending out of the distal end portion of the device guide support.

2. The surgical device guide of claim 1, in further combination with:

a lock member configured to attach to the device guide support, the lock member comprising an insert with first and second semi-circular detachable members; and a dock member configured to attach to the device guide support, the dock member comprising an insert with first and second semi-circular detachable members.

3. The surgical device guide of claim 1, wherein the open channel has a diameter in a range of about 1-6 mm.

4. The surgical device guide of claim 3, wherein the open channel has a diameter in a range of about 2-3 mm.

5. The surgical device guide of claim 1, wherein the first and second semi-circular members have a wall with edges thereof being planar and configured to releasably abut each other to encircle the through channel, and wherein the first and second semi-circular members have one end portion that is tapered.

6. A trajectory frame assembly, comprising:

a base having a patient access aperture formed therein, wherein the base is configured to be secured to the body of a patient;

a yoke movably mounted to the base and rotatable about a roll axis;

a platform movably mounted to the yoke and rotatable about a pitch axis;

an elongated device guide support secured to the platform, wherein the device guide support comprises opposite proximal and distal end portions, wherein the device guide support comprises a bore therethrough that extends from the proximal end portion to the distal end portion;

a lock member releasably attached to the proximal end portion of the device guide support;

a dock member that resides below the lock member and that releasably engages the lock member; and a device guide extending through the device guide support, wherein the device guide has two elongate cooperating rigid members that define a longitudinally extending through-channel with longitudinally split lines when held in the device guide support and that can laterally separate from each other along the longitudinally split lines upon removal from the device guide support.

7. The assembly of claim 6, wherein the lock member resides above, axially in line with the dock member and comprises an outer housing that holds an insert, wherein the insert has first and second releasably attached segments that form a longitudinally extending open channel when attached together.

8. The assembly of claim 6, wherein the dock member comprises an outer housing that holds an insert, wherein the insert has first and second releasably attached segments that form a longitudinally extending open channel when attached together.

9. A surgical assembly for image guided surgery comprising:
a device guide support adapted to attach to a trajectory guide frame, the device guide support having opposite proximal and distal end portions and comprising a cylindrical, longitudinally extending open channel;
a dock member configured to engage the device guide support;
a lock member configured to attach to the dock member above the device guide support;
a removable guide support cap configured to attach to a top of the device guide support under the dock member; and
a surgical device guide releasably held inside the device guide support, the surgical device guide comprising first and second elongate semi-circular members that cooperate to define a longitudinally extending open channel and that separate along longitudinally extending split lines into discrete first and second elongate semicircular members, wherein the first and second elongate semi-circular members have a fixed common shape both when attached and when separated, and wherein the surgical device guide has a length with a lower end portion extending out of the distal end portion of the device guide support,
wherein the lock member comprises a lock member outer housing, wherein the dock member comprises a dock member outer housing, wherein the lock member outer housing and the dock member outer housing each comprise respective inserts held therein, and wherein each of the respective inserts comprise cooperating first and second longitudinally extending members that define an open longitudinally extending channel and that can separate from each other when removed from the trajectory guide support.

10. The assembly of claim 9, further comprising a device guide held in the device guide support, wherein the device guide includes first and second longitudinally members with an arcuate wall with planar outer edges that cooperate to define an open longitudinally extending through-channel when held in the device guide support, wherein the planar outer edges are configured to releasably abut each other to form a cylindrical body and enclose the channel, and wherein the channel has a diameter in a range of about 1-6 mm.

11. The assembly of claim 9, wherein the channel has a diameter in a range of about 2-3 mm.

12. A trajectory frame assembly with a trajectory frame comprising a tubular device guide support that extends through a platform of the trajectory frame along a Z-direction and includes opposite proximal and distal end portions with a longitudinally extending bore, wherein the device guide support releasably holds a device guide with a distal end portion that is adapted to be positioned proximate a patient access aperture, wherein the device guide includes a longitudinally extending bore therethrough that is smaller than the device guide support bore, wherein the device guide is rigid and has cooperating first and second segments with longitudinally extending split lines that reside partially inside the tubular device guide support and that can be separated along the longitudinally extending split lines once removed from the tubular device guide support, and wherein the device guide has a length with a lower end portion extending out of the distal end portion of the device guide support.

13. The trajectory frame assembly of claim 12, wherein the first and second segments of the device guide cooperate and face each other to define the bore of the device guide, and wherein the first and second segments have a length sufficient to place a lower end portion thereof outside the distal end portion of the tubular device guide support and cooperatively engage to have a diameter in a range of about 1-6 mm.

14. The trajectory frame assembly of claim 13, wherein the bore of the device guide has a diameter in a range of about 2-3 mm, and wherein the assembly further comprises a peel-away sheath held in the bore of the device guide and extending a distance above the device guide.

15. A method of placing an implantable device in a patient, comprising: providing a trajectory frame releasably holding the surgical device guide and the guide support of claim 1; guiding placement of the surgical device guide to a desired interbody location using the trajectory frame; inserting the implantable device through the surgical device guide and into the patient at the desired interbody location; and then slidably removing the surgical device guide out of the guide support and separating the surgical device guide into the first and second elongate semi-circular members while leaving the implantable device in position in the patient.

16. The method of claim 15, wherein the guide support comprises a dock attached to the guide support and a lock attached to the dock to hold the dock to the guide support, wherein the dock and lock each include a respective insert with first and second cooperating, detachable longitudinally extending members, the method further comprising before the step of slidably removing the surgical device guide, slidably removing the lock insert from the lock and separating the first and second cooperating members thereof, then slidably removing the dock insert from the dock and separating the first and second cooperating members thereof.

17. The method of claim 15, wherein the device that is implanted comprises an implantable lead with greater than four electrodes and less than 200 electrodes.

* * * * *